(12) United States Patent
Yi

(10) Patent No.: US 7,341,721 B2
(45) Date of Patent: Mar. 11, 2008

(54) β₂-MICROGLOBULIN (β₂M) AND ANTI-β₂M BINDING AGENTS AS ANTI-CANCER THERAPEUTICS

(75) Inventor: Qing Yi, Little Rock, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 701 days.

(21) Appl. No.: 10/410,798

(22) Filed: Apr. 10, 2003

(65) Prior Publication Data
US 2003/0194401 A1 Oct. 16, 2003

Related U.S. Application Data

(60) Provisional application No. 60/372,049, filed on Apr. 12, 2002.

(51) Int. Cl.
A61K 31/395 (2006.01)
(52) U.S. Cl. .................................. 424/130.1; 424/174.1
(58) Field of Classification Search .............. 424/130.1
See application file for complete search history.

(56) References Cited

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Gura (Science, 1997, 278:1041-1042.).*
Jain (Scientific American Jul. 1994).*
Dillman (Annals of Internal Medicine, vol. 111, pp. 592-603, 1989).*
Weiner (Seminars Oncology, vol. 26, No. 4, 1999, pp. 41-50).*
Durie et al (Blood, 1990, 75(4):823-830).*
Alexanian, R. et al., The Treatment of Multiple Myeloma, *New England Journal of Medicine*, 330, 484-489, 1994.
Barlogie, B., Plasma Cell Myeloma, In: E. Beutler, M. Lichtman, B. Coller, and T. Kipps, (eds.) In *William's Hematology*, Fifth Edition, New York: McGraw-Hill, 1109-1126, 1995.
Barlogie, B. et al., Total Therapy with Tandem Transplants for Newly Diagnosed Multiple Myeloma, *Blood*, 93, 55-65, 1999.
Bataille, R. et al., Beta-2-Microglobulin in Myeloma: Optimal Use for Staging, Prognosis, and Treatment—a Prospective Study of 160 Patients, *Blood*, 63, 468-476, 1984.
Bataille, R. et al., In Vitro Production of Beta-2-Microglobulin by Human Myeloma Cells, *Cancer Investigation*, 6, 271-277, 1988.
Bjorkman, P. J. et al., Structure, Function and Diversity of Class I Major Histocompatibility Molecules, *Annual Review of Biochemistry*, 59, 253-288, 1990.
Blackman, M. et al., The Role of the T Cell Receptor in Positive and Negative Selection of Developing T Cells, *Science*, 248, 1335-1341, 1990.
Bratton, S. B. et al., Protein Complexes Activate Distinct Cascades in Death Receptor and Stress-Induced Apoptosis, *Experimental Cell Research*, 256, 27-33, 2000.
Brenning, G. et al., The Effect of Alpha and Gamma-Interferon on Proliferation and Production of IgE and beta 2-microglobulin in the Human Myeloma Cell Line U266 and in an Alpha-Interferon resistant U266 Subline, *Sandinavian Journal of Haematology*, 37, 280-288, 1986.
Bunning, R. A. et al., Serum β₂-Microglobulin Levels in Urological Cancer, *Journal of Urology*, 121, 624-625, 1979.
Campos, L. et al., Serum β₂-Microglobulin in Adult Myeloid Acute Leukemias, *Blut*, 48, 221-226, 1984.
Cuzik, J. et al., The Prognostic Value of Serum β₂-Microglobulin Compared with Other Presentation Features in Myelomatosis, *British Journal of Cancer*, 52, 1-6, 1985.
Demaria, S. et al., CD8 and β₂-Microglobulin-Free MHC Class I Molecules in T Cell Immunoregulation, *International Journal of Clinical and Laboratory Research*, 23, 61-69, 1993.
Genestier, L. et al., T Cell Sensitivity to HLA Class I-Mediated Apoptosis Is Dependent on Interleukin-2 and Interleukin-4, *European Journal of Immunology*, 27, 495-499, 1997.
Georgii-Hemming et al., Insulin-Like Growth Factor I Is a Growth and Survival Factor in Human Multiple Myeloma Cell Lines, *Blood*, 88, 2250-2258, 1996.
Gratzner, H. G., Monoclonal Antibody to 5-Bromo- and 5-Iododeoxyuridine: a New Reagent for Detection of DNA Replication, *Science*, 218, 474-475, 1982.
Grieco, M. H. et al., Elevated β₂-Microglobulin and Lysozyme Levels in Patients with Acquired Immune Deficiency Syndrome, *Clinical Immunology and Immunopathology*, 32, 174-184, 1984.
Grigorieva, I. et al., The Bone Marrow Stromal Environment Is a Major Factor in Myeloma Cell Resistance to Dexamethasone, *Experimental Hematology*, 26, 597-603, 1998.
Hallek, M. et al., Multiple Myeloma: Increasing Evidence for a Multistep Transformation Process, *Blood*, 91, 3-21, 1998.
Hardin, J. et al., Interleukin-6 Prevents Desamethasone-Induced Myeloma Cell Death, *Blood*, 84, 3063-3070, 1994.
Hyafil, F. et al., Dissociation and Exchange of the Beta2-Microglobulin Subunit of HLA-A and HLA-B Antigens, *Proceeding of the National Academy of Sciences USA*, 76, 5834-5838, 1979.
Karlsson, F. A. et al., β₂-Microglobulin in Clinical Medicine, *Scandinavian Journal of Clinical and Laboratory Investigation*, 40, S27-S37, 1980.
Kawano, M. et al., Autocrine Generation and Requirement of BSF-2/IL-6 for Human Multiple Myeloma, *Nature*, 332, 83-85, 1988.

(Continued)

Primary Examiner—Misook Yu
Assistant Examiner—Sean E Aeder
(74) Attorney, Agent, or Firm—Kilpatrick Stockton LLP

(57) ABSTRACT

The present invention describes the use of agents that interact with major histocompatibility complex (MHC) HLA class I molecules, such as β₂-microglobulin, or antibodies that bind to β₂-microglobulin, for the treatment and prevention of multiple myeloma and other types of cancer. The anti-cancer therapeutics of the present invention interact with MHC molecules on the surface of the tumor cell to increase apoptosis and inhibit cell growth and proliferation. For example, in an embodiment, anti-β₂-microglobulin antibodies inhibit the growth of multiple myeloma cells by over 90%. Thus, the present invention describes a new class of anti-cancer therapeutics and methods of use.

21 Claims, 20 Drawing Sheets

OTHER PUBLICATIONS

Kuby, J., Major Histocompatibility Complex, In: J. Kuby (ed.), *Immunology*, Third Edition, New York: W. H. Freeman, 223-262, 1997.

Ladasky, J. J. et al., Residue 3 of $\beta_2$-Microglobulin Affects Binding of Class I MHC Molecules by the W6/32 Antibody, *Immunogenetics*, 49, 312-320, 1999.

Liabeuf, A. et al., An Antigenic Determinant of Human $\beta_2$-Microglobulin Masked by the Association with HLA Heavy Chains at the Cell Surface: Analysis Using Monoclonal Antibodies, *Journal of Immunology*, 127, 1542-1548, 1981.

Lifson, A. R. et al., Serum $\beta_2$-Microglobulin and Prediction of Progression to AIDS in HIV Infection, *Lancet*, 339, 1436-1440, 1992.

Ljunggren, H. G et al., In Search of the "Missing Self": MHC Molecules and NK Cell Recognition, *Immunol. Today*, 11, 237-244, 1990.

Menaa, C. et al., Tumor Necrosis Factor Mediates the Stimulatory Effect of $\beta_2$-Microglobulin on Osteoclast Formation, *American Society for Bone and Mineral Research, 23rd Meeting Abstract Book*, p. 17 (absr), 2001.

Min, R. et al., $\beta_2$-Microglobulin as a Negative Growth Regulator of Myeloma Cells, *British Journal of Haematology*, 118, 495-505, 2002.

Mori, M. et al., $\beta_2$-Microglobulin Identified as an Apoptosis-Inducing Factor and Its Characterization, *Blood*, 94, 2744-2753, 1999.

Mori, M., Antitumor Effect of $\beta_2$-Microglobulin in Leukemic Cell-Bearing Mice via Apoptosis-Inducing Activity: Activation of Caspase-3 and Nuclear Factor-$\kappa B^1$ *Cancer Res.*, 61, 4414-4417, 2001.

Parker, K. C. et al., Subunit Interactions of Class I Histocompatibility Antigens, *Biochemistry*, 24, 5543-5550, 1985.

Revillard, J. P. et al., Structure and Metabolism of $\beta_2$-Microglobulin. *Contribution in Nephrology*, 62, 44-53, 1988.

Revillard, J. P. et al., $\beta_2$-Microglobulin and $\beta_2$-Microglobulin-Binding Proteins in Inflammatory Diseases, *European Journal of Rheumatology and Inflammation*, 5, 398-405, 1982.

Rock, K. L. et al., Dissociation of $\beta_2$-Microglobulin Leads to the Accumulation of a Substantial Pool of Inactive Class I MHC Heavy Chains on the Cell Surface, *Cell*, 65, 611-620, 1991.

Schardijn, G. H. et al., $\beta_2$-Microglobulin: Its Significance in the Evaluation of Renal Function, *Kidney International*, 32, 635-641, 1987.

Skov, S., Intracellular Signal Transduction Mediated by Ligation of MHC Class I Molecules, *Tissue Antigens*, 51, 215-223, 1998.

Skov, S. et al., Ligation of Major Histocompatability Complex (MHC) Class I Molecules on Human T Cells Induces Cell Death through PI-3 Kinase-Induced c-Jun $NH_2$-Terminal Kinase Activity: a Novel Apoptotic Pathway Distinct from Fas-Induced Apoptosis, *Journal of Cell Biology*, 139, 1523-1531, 1997.

Smith, M. H. et al., The Conformational Flexibility of Class I H-2 Molecules as Revealed by Anti-Peptide Antibodies Specific for Intracytoplasmic Determinants: Differential reactivity of $\beta_2$-Microglobulin "Bound" and "Free" H2Kb Heavy chains, *Molecular Immunology*, 27, 169-180, 1990.

Sprague, S. M. et al., Is $\beta_2$-Microglobulin a Mediator of Bone Disease? *Kidney Int.*, 47, 1-6, 1995.

Townsend, A. R. et al., Antigen Recognition by Class I—Restricted T Lymphocytes, *Annua. Review of Immunology*, 7, 601-624, 1989.

Vermes, I. et al., A Novel Assay for Apoptosis: Flow Cytometric Detection of Phosphatidylserine Expression on Early Apoptotic Cells Using Fluorescein Labeled Annexin V., *Journal of Immunological Methods*, 184, 39-51, 1995.

Walters, M. T. et al., Comparison of Serum and Synovial Fluid Concentrations of $\beta_2$-Microglobulin and C Reactive Protein in Relation to Clinical Disease Activity and Synovial Inflammation in Rheumatoid Arthritis, *Annual of Rheumtological Diseases*, 48, 905-911, 1989.

Woodle, E. S. et al., Anti-Human Class I MHC Antibodies Induce Apoptosis by a Pathway That Is Distinct from the Fas Antigen-Mediated Pathway, *Journal of Immunology*, 158, 2156-2164, 1997.

Yaccoby, S. et al., Myeloma Interacts with the Bone Marrow Microenvironment to Induce Osteoclastogenesis and Is Dependent on Osteoclast Activity, *British Journal of Haematology*, 116:278-290, 2002.

Yi, Q. et al., Levels of $CD5^{30}$ B Lymphocytes Do Not Differ between Patients with Myasthenia Gravis and Healthy Individuals, *Neurology*, 42, 1081-1084, 1992.

Yi, Q. et al., Myeloma Bone Marrow Plasma Cells: Evidence for Their Capacity as Antigen-Presenting Cells, *Blood*, 90, 1960-1967, 1997.

International Search Report mailed Oct. 17, 2003 corresponding to PCT/US02/11734.

O'Brien et al., The CA 125 Gene: An Extracellular Superstructure Dominated by Repeat Sequences; Tumor Biology, 2001, vol. 22, pp. 348-366.

Yin et al., Molecular Cloning of the CA125 Ovarian Cancer Antigen; The Journal of Biological Chemistry, Jul. 20, 2001, vol. 276, No. 29, pp. 27371-27375.

Argueso et al., MUC16 Mucin is Expressed by the Human Ocular Surface Epithelia and Carries the H185 Carbohydrate Epitope, Investigative Ophthalmology & Visual Science, Jun. 2003, vol. 44, No. 6, pp. 2487-2495.

Cunningham, B. et al. "The Complete Amino Acid Sequence of $\beta_2$-Microglobulin." Biochemistry, 1973, vol. 12, No. 24, pp. 4811-4821.

Johnstone, A. et al., "Immunochemistry in Practice." Blackwell Scientific Publications, Oxford, 1987, pp. 49-50.

Patent Cooperation Treaty, International Search Report, International Application No. PCT/US03/11184, mailed on Jul. 5, 2005, 7 pages.

Altun, M. et al., "Effects of PS-341 on the Activity and Composition of Proteasomes in Multiple Myeloma Cells," Cancer Res., vol. 65, No. 17, pp. 7896-7901, 2005.

Bajenova, O. et al., "RIP Kinase is Involved in Arsenic-Induced Apoptosis in Multiple Myeloma Cells," Apoptosis, vol. 9, No. 5, pp. 561-571, 2004.

Baughn, L. et al., "A Novel Orally Active Small Molecule Potently Induces $G_1$ Arrest in Primary Myeloma Cells and Prevents Tumor Growth by Specific Inhibition of Cyclin-Dependent Kinase 4/6," Cancer Res., vol. 66, No. 15, pp. 7661-7667, 2006.

Bonner, J. et al., "Radiotherapy Plus Cetuximab for Squamous-Cell Carcinoma of the Head and Neck," New England Journal of Medicine, vol. 354, pp. 567-578, 2006.

Catley, L. et al., "Aggresome Induction by Proteasome Inhibitor Bortezomib and $\alpha$-tubulin Hyperacetylation by Tubulin Deacetylase (TDAC) Inhibitor LBH589 are Synergistic in Myeloma Cells," Blood First Edition Paper, prepublished online Jun. 13, 2006; DOI 10.1182/blood-2006-04-016055.

Chauhan, D. et al., "A Novel Carbohydrate-Based Therapeutic GCS-100 Overcomes Bortezomib Resistance and Enhances Dexamethasone-Induced Apoptosis in Multiple Myeloma Cells," Cancer Res., vol. 65, No. 18, pp. 8350-8358, 2005.

Chauhan, D. et al., "A Novel Orally Active Proteasome Inhibitor Induces Apoptosis in Multiple Myeloma Cells with Mechanisms Distinct from Bortezomib," Cancer Cell, vol. 8, pp. 407-419, 2005.

Cheson, B., "Monoclonal Antibody Therapy for B-Cell Malignancies," Semin. Oncol., vol. 33, Suppl. 5, pp. S2-S14, 2006.

Chiriva-Internati, M. et al., "Myeloma-Reactive Allospecific Cytotoxic T Lymphocytes Lyse Target Cells via the Granule Exocytosis Pathway," British Journal of Haematology, vol. 112, pp. 410-420, 2001.

Coiffier, B., "Monoclonal Antibody as Therapy for Malignant Lymphomas," C.R. Biologies, vol. 329, pp. 241-254, 2006.

Cunningham, D. et al., "Cetuximab Monotherapy and Cetuximab plus Irinotecan in Irinotecan-Refractory Metastatic Colorectal Cancer," New England Journal of Medicine, vol. 351, pp. 337-345, 2004.

Fassas, A. et al., "Tamoxifen-based Treatment Induces Clinically Meaningful Responses in Multiple Myeloma Patients with Relapsing Disease after Autotransplantation," Leukemia & Lymphoma, vol. 42, pp. 1323-1328, 2001.

Feinman, R. et al., "Role of NF-κB in the Rescue of Multiple Myeloma Cells from Glucocorticoid-Induced Apoptosis by Bcl-2," Blood, vol. 93, No. 9, pp. 3044-3052, 1999.

Haber, D., "Researchers May Use Cancer Cell Lines to Identify Target Populations Prior to Clinical Trials," Journal of the National Cancer Institute, vol. 98, No. 12, pp. 810-811, 2006.

Hamasaki, M. et al., "Azaspirane (N-N-diethyl-8,8-dipropyl-2-azaspiro[4.5] decane-2-propanamine) inhibits Human Multiple Myeloma Cell Growth in the Bone Marrow Milieu In Vitro and In Vivo," Blood, vol. 105, No. 11, pp. 4470-4476, 2005.

Hideshima, T. et al., "Perifosine, an Oral Bioactive Novel Alkylphospholipid, inhibits Akt and Induces In Vitro and In Vivo Cytotoxicity in Human Multiple Myeloma Cells," Blood, vol. 107, No. 10, pp. 4053-4062, 2006.

Hideshima, T. et al., "Small-Molecular Inhibition of Proteasome and Aggresome Function induces Synergistic Antitumor Activity in Multiple Myeloma," PNAS, vol. 102, No. 24, pp. 8567-8572, 2005.

Ishitsuka, K. et al., "Novel Inosine Monophosphate Dehydrogenase Inhibitor VX-944 Induces Apoptosis in Multiple Myeloma Cells Primarily Via Caspase-Independent AIF/Endo G Pathway," Oncogene, vol. 24, pp. 5888-5896, 2005.

Kaminski, M. et al., "Radioimmunotherapy of B-Cell Lymphoma with [$^{131}$I] Anti-B1 (Anti-CD20) Antibody," New England Journal of Medicine, vol. 329, vol. 7, pp. 459-465, 1993.

Lin, M. et al., "The Evolution of Antibodies into Versatile Tumor-Targeting Agents," Clinical Cancer Research, vol. 11, pp. 129-138, 2005.

Mahtouk, K. et al., "An Inhibitor of the EGF Receptor Family Blocks Myeloma Cell Growth Factor Activity of HB-EGF and Potentiates Dexamethasone or Anti-IL-6 Antibody-Induced Apoptosis," Blood, vol. 103, No. 5, pp. 1829-1837, 2004.

Mahtouk, K. et al., "Expression of EGF-Family Receptors and Amphiregulin in Multiple Myeloma. Amphiregulin is a Growth Factor for Myeloma Cells," Oncogene, vol. 24, pp. 3512-3524, 2005.

Meinhardt, G. et al., "Treosulfan is an Effective Inducer of Cell Death in Myeloma Cell Lines and Primary Myeloma Cells from Patients," British Journal of Haematology, vol. 122, pp. 892-899, 2003.

Ni, H. et al., "Protein Kinase C-Delta is Commonly Expressed in Multiple Myeloma Cells and its Downregulation by Rottlerin Causes Apoptosis," British Journal of Haematology, vol. 121, pp. 849-856, 2003.

Piccart-Gebhart, M. et al., "Trastuzumab after Adjuvant Chemotherapy in HER2-Positive Breast Cancer," New England Journal of Medicine, vol. 353, pp. 1659-1672, 2005.

Raje, N. et al., "Seliciclib (CYC202 or R-roscovitine), a Small-Molecular Cyclin-Dependent Kinase Inhibitor, Mediates Activity via Down-Regulation of Mcl-1 in Multiple Myeloma," Blood, vol. 106, No. 3, pp. 1042-1047.

Ren, S. et al., "Adenoviral-Mediated Transfer of Human Wild-Type p53, GM-CSF and B7-1 Genes Results in Growth Suppression and Autologous Anti-Tumor Cytotoxicity of Multiple Myeloma Cells In Vitro," Cancer Immunol. Immunother., vol. 55, pp. 375-385, 2006.

Roccaro, A. et al., "Bortezomib Mediates Antiangiogenesis in Multiple Myeloma via Direct and Indirect Effects on Endothelial Cells," Cancer Res., vol. 66, No. 1, pp. 184-191, 2006.

Ross, J. et al., "Antibody-Based Therapeutics in Oncology," Expert Rev. Anticancer Ther., vol. 3, No. 1, pp. 107-121, 2003.

Siegel, D. et al., "Hexamethylene Bisacetamide Induces Programmed Cell Death (Apoptosis) and Down-Regulates BCL-2 Expression in Human Myeloma Cells," Proc. Natl. Acad. Sci. USA, vol. 95, pp. 162-166, 1998.

Slamon, D. et al., "Use of Chemotherapy Plus A Monoclonal Antibody against HER2 for Metastatic Breast Cancer that Overexpresses HER2," New England Journal of Medicine, vol. 344, No. 11, pp. 783-792, 2001.

Stern, M. et al., "Overview of Monoclonal Antibodies in Cancer Therapy, Present and Promise," Critical Reviews in Oncology/Hematology, vol. 54, pp. 11-29, 2005.

Tai, Y. et al., "Human Anti-CD40 Antagonist Antibody Triggers Significant Antitumor Activity against Human Multiple Myeloma," Cancer Res., vol. 65, No. 13, pp. 5898-5906, 2005.

Tai, Y et al., "Immunomodulatory Drug Lenalidomide (CC-5013, IMiD3) Augments Anti-CD-40 SGN-40-Induced Cytotoxicity in Human Multiple Myeloma: Clinical Implication," Cancer Res., vol. 65, No. 24, pp. 11712-11720, 2005.

Tai, Y. et. al., "Role of B-Cell-Activating Factor in Adhesion and Growth of Human Multiple Myeloma Cells in the Bone Marrow Microenvironment," Cancer Res., vol. 66, No. 13, pp. 6675-6682, 2006.

Tassone, P. et al., "Combination Therapy with Interleukin-6 Receptor Superantagonist Sant7 and Dexamethasone induces Antitumor Effects in a Novel SCID-hu In Vivo Model of Human Multiple Myeloma," Clin. Cancer Res., vol. 11, No. 11, pp. 4251-4258, 2005.

Trudel, S. et al., "CHIR-258, A Novel, Multitargeted Tyrosine Kinase Inhibitor for the Potential Treatment of t(4;14) Multiple Myeloma," Blood, vol. 105, No. 7, pp. 2941-2948, 2005.

Uno, T. et al., "Eradication of Established Tumors in Mice by a Combination Antibody-Based Therapy," Nature Medicine, vol. 12, No. 6, pp. 693-698, 2006.

Wang, Z. et al., "Sp17 Gene Expression in Myeloma Cells is Regulated by Promoter Methylation," British Journal of Cancer, vol. 91, pp. 1597-1603, 2004.

Yang, J. et al., "A Randomized Trial of Bevacizumab, an Anti-Vascular Endothelial Growth Factor Antibody, for Metastatic Renal Cancer," New England Journal of Medicine, vol. 349, No. 5, pp. 427-434, 2003.

Yasui, H. et al., "SDX-101, the R-enantiomer of Etodolac, Induces Cytotoxicity, Overcomes Drug Resistance, and Enhances the Activity of Dexamethasone in Multiple Myeloma," Blood, vol. 106, No. 2, pp. 706-712, 2005.

Yasui, H. et al., "FTY720 Induces Apoptosis in Multiple Myeloma Cells and Overcomes Drug Resistance," Cancer Res., vol. 65, No. 16, pp. 7478-7484, 2005.

Zangemeister-Wittke, U., "Antibodies for Targeted Cancer Therapy—Technical Aspects and Clinical Perspectives," Pathobiology, vol. 72, No. 6, pp. 279-286, 2005.

Gazitt, Y. et al., "Bcl-2 Overexpression is Associated with Resistance to Dexamethasone, but not Melphalan, in Multiple Myeloma Cells," International Journal of Oncology, vol. 13, No. 2, pp. 397-405, 1998.

* cited by examiner

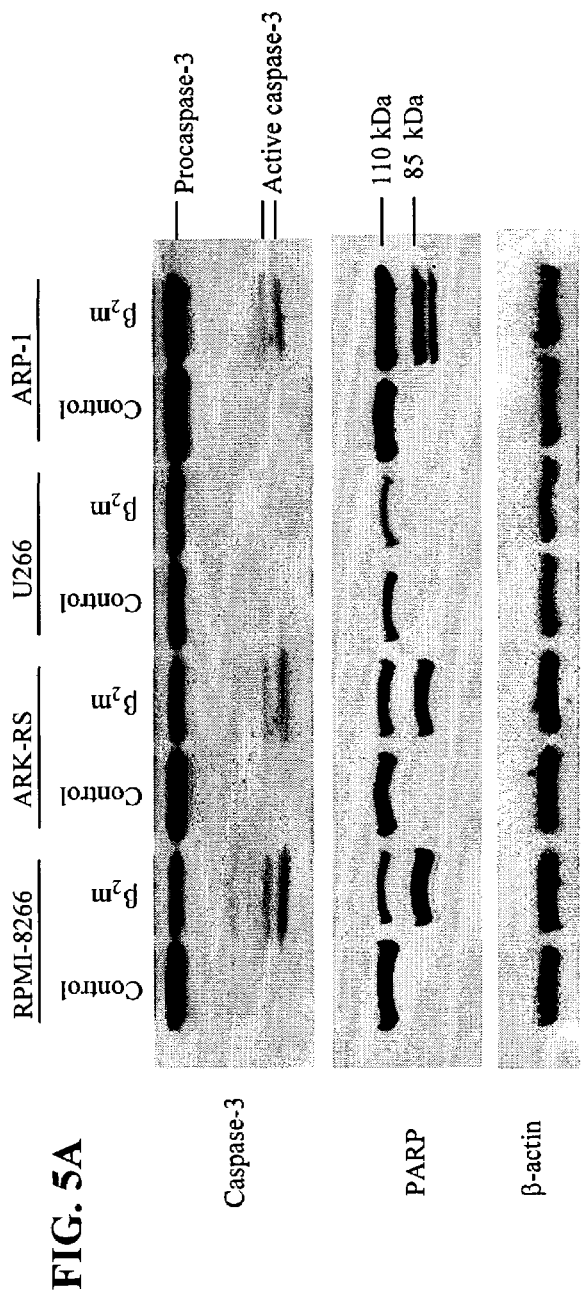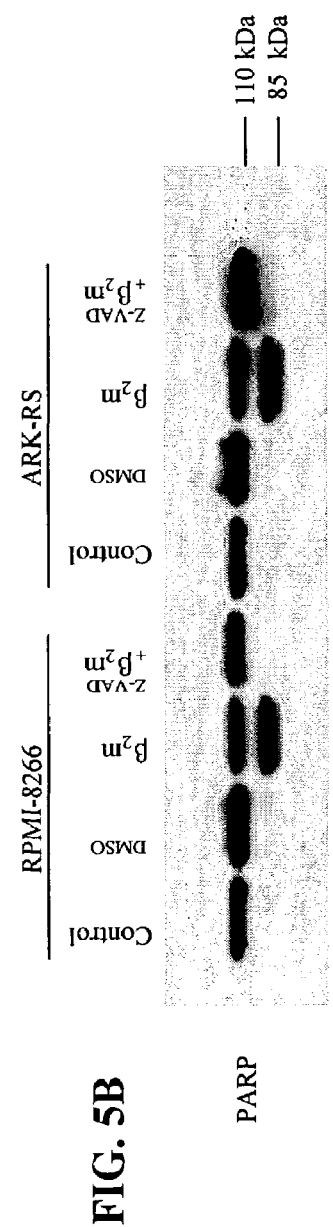
FIG. 5A
FIG. 5B

US 7,341,721 B2

$\beta_2$-MICROGLOBULIN ($\beta_2$M) AND ANTI-$\beta_2$M BINDING AGENTS AS ANTI-CANCER THERAPEUTICS

PRIORITY CLAIM

This application claims priority to U.S. Provisional application No. 60/372,049, filed Apr. 12, 2002. The disclosure of U.S. Provisional application No. 60/372,049, is hereby incorporated by reference in its entirety.

FIELD OF THE INVENTION

The present invention relates to the field of anti-cancer therapeutics. For example, the present invention describes the use of agents that interact with major histocompatibility complex (MHC) HLA class I molecules, such as antibodies that bind to $\beta_2$-microglobulin, for the treatment and prevention of multiple myeloma and other types of cancer.

BACKGROUND OF THE INVENTION

Cancer remains the second leading cause of death in the western hemisphere. While some types of cancer may be managed by surgery, radiation therapy and/or chemotherapy, other types of cancer are considered to be incurable.

For example, multiple myeloma (MM) is a B-cell neoplasm characterized by the accumulation of malignant plasma cells in the bone marrow. Multiple myeloma accounts for about 1% of all cancers and about 10% of all hematological malignancies. The American Cancer Society estimated that about 14,600 new cases of myeloma would be diagnosed and nearly 11,000 Americans would die from multiple myeloma in 2002. Although high-dose chemotherapy followed by autologous stem cell support may result in remission for about 50% of individuals with MM, relapses are still frequent (Barlogie B., et al., *Blood,* 93:55-65, 1999).

Thus, there is a need for better treatment modalities for multiple myeloma and other types of cancer. What is needed in cancer prevention and therapeutics are ways to either prevent tumors from forming, or to inhibit the growth of tumors once formed. Also, what is needed are agents that act specifically at the tumor cell, thus minimizing non-specific and/or toxic side effects. Preferably, the chemotherapeutic agents will comprise agents that target the cancer cells with high efficacy to either reduce cellular signals that promote cell growth, or to increase cellular signals that promote cell death.

SUMMARY

The present invention describes the use of agents that interact with major histocompatibility complex (MHC) HLA class I molecules on the surface of tumor cells for the treatment of cancer. Embodiments of the present invention recognize that $\beta_2$-microglobulin and antibodies to $\beta_2$-microglobulin may interact with MHC molecules on tumor cells to inhibit the growth and proliferation of the tumor.

Thus, in one aspect, the present invention comprises a composition to reduce tumor growth or proliferation in an individual in need thereof comprising a pharmacologically effective amount of an agent that interacts with MHC $\beta_2$-microglobulin HLA class I molecules located on the tumor cell surface in a pharmaceutically acceptable carrier, wherein a pharmacologically effective amount of the agent comprises sufficient agent to reduce proliferation of the tumor cells.

In another aspect, the present invention comprises a composition to reduce tumor growth or proliferation in an individual in need thereof comprising a pharmacologically effective amount of an agent that binds to $\beta_2$-microglobulin ($\beta_2$m) in a pharmaceutically acceptable carrier, wherein a pharmacologically effective amount of the $\beta_2$-microglobulin binding agent comprises sufficient agent to reduce proliferation of the tumor cells.

In another aspect, the present invention comprises a method to reduce tumor growth or proliferation in an individual in need thereof comprising application of a pharmacologically effective amount of an agent that interacts with MHC $\beta_2$-microglobulin HLA class I molecules located on the tumor cell surface in a pharmaceutically acceptable carrier, wherein a pharmacologically effective amount of the agent comprises sufficient agent to reduce proliferation of the tumor cells.

In another aspect, the present invention comprises a method to reduce tumor growth or proliferation in an individual in need thereof comprising application of a pharmacologically effective amount of an agent that binds to $\beta_2$-microglobulin ($\beta_2$m) in a pharmaceutically acceptable carrier to the individual, wherein a pharmacologically effective amount of the $\beta_2$-microglobulin binding agent comprises sufficient agent to reduce proliferation of the tumor cells.

In yet another aspect, the present invention comprises a kit to reduce tumor growth or proliferation in an individual in need thereof comprising:

(a) at least one container comprising a pharmacologically effective amount of an agent that interacts with MHC $\beta_2$-microglobulin HLA class I molecules located on the tumor cell surface, wherein a pharmacologically effective amount of said agent comprises sufficient agent to reduce proliferation of said tumor cells;

(b) a pharmaceutically acceptable carrier, and (c) instructions for use.

From the foregoing summary, it is apparent that an object of the present invention is to provide methods and compositions for the use of agents that are able to interact with MHC class I molecules on the surface of tumor cells as anti-cancer therapeutics. It is also an object of the present invention to provide compositions and methods for the treatment of multiple myeloma. There are, of course, additional features of the invention which will be described hereinafter and which will form the subject matter of the claims appended hereto. It is to be understood that the invention is not limited in its application to the specific details as set forth in the following description and figures. The invention is capable of other embodiments and of being practiced or carried out in various ways.

DETAILED DESCRIPTION OF THE INVENTION

Figure 1:
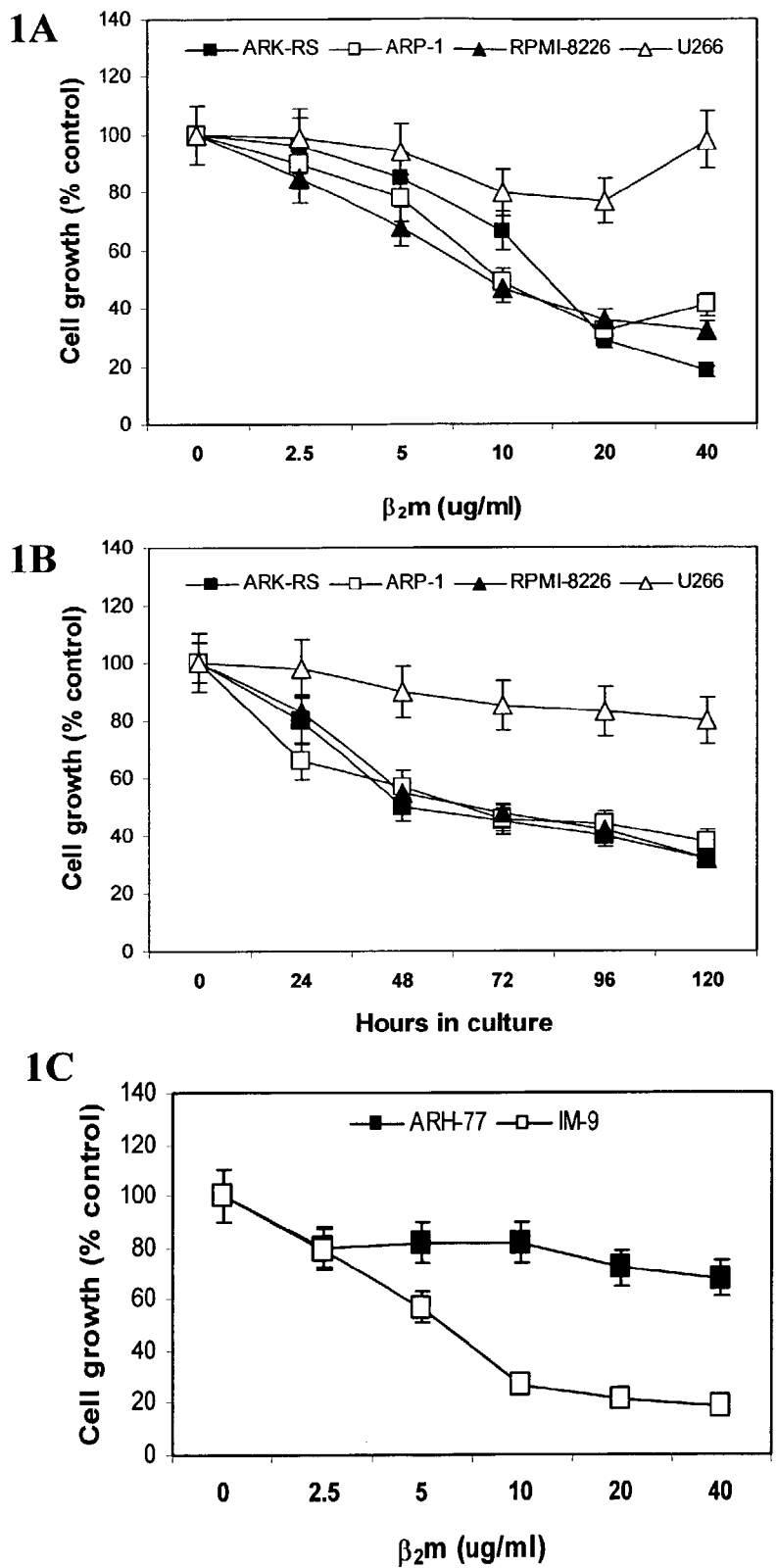
FIG. 1 illustrates the cellular effects of $\beta_2$m on growth of myeloma cells in accordance with an embodiment of the present invention wherein (A) shows a dose-response of four Epstein Barr Virus (EBV)-negative cell lines in a 48-hour culture; (B) shows a time-response of the EBV-negative cell lines in cultures with or without the addition of 20 µg/ml $\beta_2$m; and (C) shows a dose response of two EBV-positive cell lines in a 48-hour culture. Cell growth, determined by $^3$H-thymidine incorporation assay, is expressed as a percentage of control. Values are expressed as the mean ±SD of four experiments.

The present invention describes the use of $\beta_2$-microglobulin based therapeutics for the treatment and prevention of cancer. Thus, embodiments of the present invention recognize that $\beta_2$-microglobulin interacts with other molecules of the major histocompatibility complex (MHC) class I to affect an individual's ability to resist and combat tumor development. In one embodiment, application of exogenous $\beta_2$-microglobulin inhibits cancer cell growth and proliferation. In another embodiment, anti-$\beta_2$-microglobulin antibodies inhibit cancer cell growth and proliferation. In yet another embodiment, $\beta_2$-microglobulin enhances the ability of $\beta_2$-microglobulin antibodies to inhibit cancer cell growth and proliferation. Thus, embodiments of the present invention recognize that antibodies to $\beta_2$-microglobulin interact with $\beta_2$-microglobulin to invoke a synergistic inhibition of cancer cell growth.

In one aspect, the present invention comprises a composition to reduce tumor growth or proliferation in an individual in need thereof comprising a pharmacologically effective amount of an agent that interacts with MHC $\beta_2$-microglobulin HLA class I molecules located on the tumor cell surface in a pharmaceutically acceptable carrier, wherein a pharmacologically effective amount of the agent comprises sufficient agent to reduce proliferation of the tumor cells.

In an embodiment, the agent comprises $\beta_2$-microglobulin. Alternatively, the agent may comprise an antibody that binds $\beta_2$-microglobulin. In yet another embodiment, the agent comprises $\beta_2$-microglobulin used in combination with an antibody that binds $\beta_2$-microglobulin. Preferably, the use of both $\beta_2$-microglobulin used in combination with an antibody that binds $\beta_2$-microglobulin provides a greater than additive effect.

In an embodiment, the agent reduces growth or proliferation of the tumor cells significantly. Preferably, a pharmacologically effective amount of the agent reduces proliferation of the tumor cells by over 50%. More preferably, a pharmacologically effective amount of the agent reduces proliferation of the tumor cells by over 75%. Even more preferably, a pharmacologically effective amount of the agent reduces proliferation of the tumor cells by over 90%.

The compositions of the present invention are preferably effective against a wide variety of tumor types. Thus, in an embodiment, the cancer comprises multiple myeloma, lymphoma, leukemia, and solid tumors including, but not limited to, breast cancer, melanoma and colon cancer.

There may be multiple mechanisms by which the compositions of the present invention exert a therapeutic effect. In an embodiment, a pharmacologically effective amount of the agent binds to MHC $\beta_2$-microglobulin HLA class I molecules located on the surface of the tumor cells. Also, in an embodiment, a pharmacologically effective amount of the agent reduces the number of MHC $\beta_2$-microglobulin HLA class I molecules located on the surface of the tumor cells. Alternatively, and/or additionally, a pharmacologically effective amount of the agent stimulates apoptosis in the tumor cells. In an embodiment, stimulation of apoptosis is mediated at least in part by activation of caspases. Alternatively, and/or additionally, the agent causes changes in the cell cycle distribution of the cancer cells.

In another aspect, the present invention comprises a composition to reduce tumor growth or proliferation in an individual in need thereof comprising a pharmacologically effective amount of an agent that binds to $\beta_2$-microglobulin ($\beta_2$m) in a pharmaceutically acceptable carrier, wherein a pharmacologically effective amount of the $\beta_2$-microglobulin binding agent comprises sufficient agent to reduce proliferation of the tumor cells.

In an embodiment, the agent that binds to $\beta_2$-microglobulin ($\beta_2$m) comprises an antibody to $\beta_2$-microglobulin. Additionally, in an embodiment, the composition further comprises exogenous $\beta_2$-microglobulin. Preferably, the use of both $\beta_2$-microglobulin used in combination with an antibody that binds $\beta_2$-microglobulin provides a greater than additive effect.

In an embodiment, the agent reduces growth or proliferation of the tumor cells significantly. Preferably, a pharmacologically effective amount of the $\beta_2$-microglobulin binding agent reduces proliferation of the tumor cells by over 50%. More preferably, a pharmacologically effective amount of the $\beta_2$-microglobulin binding agent reduces proliferation of the tumor cells by over 75%. Even more preferably, a pharmacologically effective amount of the $\beta_2$-microglobulin binding agent reduces proliferation of the tumor cells by over 90%.

The compositions of the present invention are preferably effective against a wide variety of tumor types. Thus, in an embodiment, the cancer comprises multiple myeloma, lymphoma, leukemia, and solid tumors including, but not limited to, breast cancer, melanoma and colon cancer.

The composition may comprise a specific concentration of the $\beta_2$-microglobulin binding agent. For example, in the embodiment where the $\beta_2$-microglobulin binding agent comprises anti-$\beta_2$-microglobulin antibody, a pharmacologically effective amount of the antibody preferably comprises a concentration at the tumor cells of 0.5 to 5,000 µg/ml. More preferably, a pharmacologically effective amount of the antibody comprises a concentration at the tumor cells of 5 to 500 µg/ml. Even more preferably, a pharmacologically effective amount of the antibody comprises a concentration at the tumor cells of 20 to 100 µg/ml.

There may be multiple mechanisms by which the compositions of the present invention exert a therapeutic effect. In an embodiment, a pharmacologically effective amount of the $\beta_2$-microglobulin binding agent binds to MHC $\beta_2$-microglobulin HLA class I molecules located on the surface of the tumor cells. Also, in an embodiment, a pharmacologically effective amount of the $\beta_2$-microglobulin binding agent reduces the number of MHC $\beta_2$-microglobulin HLA class I molecules located on the surface of the tumor cells. Alternatively, and/or additionally, a pharmacologically effective amount of the $\beta_2$-microglobulin binding agent stimulates apoptosis in the tumor cells. In an embodiment, stimulation of apoptosis is mediated at least in part by activation of caspases. Alternatively, and/or additionally, the $\beta_2$-microglobulin binding agent causes changes in the cell cycle distribution of the cancer cells.

In another aspect, the present invention comprises a method to reduce tumor growth or proliferation in an individual in need thereof comprising application of a pharmacologically effective amount of an agent that interacts with MHC $\beta_2$-microglobulin HLA class I molecules located on the tumor cell surface in a pharmaceutically acceptable carrier, wherein a pharmacologically effective amount of the agent comprises sufficient agent to reduce proliferation of the tumor cells.

In an embodiment, the agent comprises $\beta_2$-microglobulin. Alternatively, the agent may comprise an antibody that binds $\beta_2$-microglobulin. In yet another embodiment, the agent comprises $\beta_2$-microglobulin used in combination with an antibody that binds $\beta_2$-microglobulin. Preferably, the use of $\beta_2$-microglobulin in combination with an antibody that binds $\beta_2$-microglobulin provides a greater than additive effect.

In an embodiment, the agent reduces growth or proliferation of the tumor cells significantly. Preferably, a pharmacologically effective amount of the agent reduces proliferation of the tumor cells by over 50%. More preferably, a pharmacologically effective amount of said agent reduces proliferation of the tumor cells by over 75%. Even more preferably, a pharmacologically effective amount of the agent reduces proliferation of the tumor cells by over 90%.

The methods of the present invention are preferably effective against a wide variety of tumor types. Thus, in an embodiment, the cancer comprises multiple myeloma, lymphoma, leukemia, and solid tumors including, but not limited to, breast cancer, melanoma and colon cancer.

There may be multiple mechanisms by which the methods of the present invention exert a therapeutic effect. In an embodiment, a pharmacologically effective amount of the agent binds to MHC $\beta_2$-microglobulin HLA class I molecules located on the surface of the tumor cells. Also, in an embodiment, a pharmacologically effective amount of the agent reduces the number of MHC $\beta_2$-microglobulin HLA class I molecules located on the surface of the tumor cells. Alternatively, and/or additionally, a pharmacologically effective amount of the agent stimulates apoptosis in the tumor cells. In an embodiment, stimulation of apoptosis is mediated at least in part by activation of caspases. Alternatively, and/or additionally, the agent causes changes in the cell cycle distribution of the cancer cells.

In another aspect, the present invention comprises a method to reduce tumor growth or proliferation in an individual in need thereof comprising application of a pharmacologically effective amount of an agent that binds to $\beta_2$-microglobulin ($\beta_2$m) in a pharmaceutically acceptable carrier to the individual, wherein a pharmacologically effective amount of the $\beta_2$-microglobulin binding agent comprises sufficient agent to reduce proliferation of the tumor cells.

In an embodiment, the agent that binds to $\beta_2$-microglobulin ($\beta_2$m) comprises an antibody to $\beta_2$-microglobulin. Additionally, in an embodiment, the composition further comprises exogenous $\beta_2$-microglobulin. Preferably, the use of $\beta_2$-microglobulin in combination with an antibody that binds $\beta_2$-microglobulin provides a greater than additive effect.

In an embodiment, the agent reduces growth or proliferation of the tumor cells significantly. Preferably, a pharmacologically effective amount of the $\beta_2$-microglobulin binding agent reduces proliferation of the tumor cells by over 50%. More preferably, a pharmacologically effective amount of the $\beta_2$-microglobulin binding agent reduces proliferation of the tumor cells by over 75%. Even more preferably, a pharmacologically effective amount of the $\beta_2$-microglobulin binding agent reduces proliferation of the tumor cells by over 90%.

The methods of the present invention are preferably effective against a wide variety of tumor types. Thus, in an embodiment, the cancer comprises multiple myeloma, lymphoma, leukemia, and solid tumors including, but not limited to, breast cancer, melanoma and colon cancer.

The methods of the present invention may employ a specific concentration of the $\beta_2$-microglobulin binding agent. For example, in the embodiment where the $\beta_2$-microglobulin binding agent comprises anti-$\beta_2$-microglobulin antibody, a pharmacologically effective amount of the antibody preferably comprises a concentration at the tumor cells of 0.5 to 5,000 µg/ml. More preferably, a pharmacologically effective amount of the antibody comprises a concentration at the tumor cells of 5 to 500 µg/ml. Even more preferably, a pharmacologically effective amount of the antibody comprises a concentration at the tumor cells of 20 to 100 µg/ml.

There may be multiple mechanisms by which the methods of the present invention exert a therapeutic effect. In an embodiment, a pharmacologically effective amount of the $\beta_2$-microglobulin binding agent binds to MHC $\beta_2$-microglobulin HLA class I molecules located on the surface of the tumor cells. Also, in an embodiment, a pharmacologically effective amount of the $\beta_2$-microglobulin binding agent reduces the number of MHC $\beta_2$-microglobulin HLA class I molecules located on the surface of the tumor cells. Alternatively, and/or additionally, a pharmacologically effective amount of the $\beta_2$-microglobulin binding agent stimulates apoptosis in the tumor cells. In an embodiment, stimulation of apoptosis is mediated at least in part by activation of caspases. Alternatively, and/or additionally, the $\beta_2$-microglobulin binding agent causes changes in the cell cycle distribution of the cancer cells.

In another aspect, the present invention comprises a kit to reduce tumor growth or proliferation in an individual in need thereof comprising:

(a) at least one container comprising a pharmacologically effective amount of an agent that interacts with MHC $\beta_2$-microglobulin HLA class I molecules located on the tumor cell surface, wherein a pharmacologically effective amount of the agent comprises sufficient agent to reduce proliferation of the tumor cells;

(b) a pharmaceutically acceptable carrier, and (c) instructions for use.

In an embodiment, the agent comprises $\beta_2$-microglobulin. Also in an embodiment, the agent comprises an antibody that binds $\beta_2$-microglobulin. In yet another embodiment, the agent comprises $\beta_2$-microglobulin used in combination with an antibody that binds $\beta_2$-microglobulin.

The kits of the present invention are preferably effective against a wide variety of tumor types. Thus, in an embodiment, the cancer comprises multiple myeloma, lymphoma, leukemia, and solid tumors including, but not limited to, breast cancer, melanoma and colon cancer.

The kits of the present invention may employ a specific concentration of the $\beta_2$-microglobulin binding agent. For example, in the embodiment where the $\beta_2$-microglobulin binding agent comprises anti-$\beta_2$-microglobulin antibody, a pharmacologically effective amount of the antibody preferably comprises a concentration at the tumor cells of 0.5 to 5,000 µg/ml. More preferably, a pharmacologically effective amount of the antibody comprises a concentration at the tumor cells of 5 to 500 µg/ml. Even more preferably, a pharmacologically effective amount of the antibody comprises a concentration at the tumor cells of 20 to 100 µg/ml.

In an embodiment, the agent reduces growth or proliferation of the tumor cells significantly. Preferably, a pharmacologically effective amount of the $\beta_2$-microglobulin binding agent reduces proliferation of the tumor cells by over 50%. More preferably, a pharmacologically effective amount of the $\beta_2$-microglobulin binding agent reduces proliferation of the tumor cells by over 75%. Even more preferably, a pharmacologically effective amount of the $\beta_2$-microglobulin binding agent reduces proliferation of the tumor cells by over 90%.

Thus, the present invention describes methods and compositions for treatment of multiple myeloma (MM) and other types of cancer. For example, the present invention describes reduction of tumor growth or proliferation by application of a composition comprising an agent that interacts with MHC $\beta_2$-microglobulin HLA class I molecules located on the tumor cell surface.

In an embodiment, the agent that interacts with MHC $\beta_2$-microglobulin HLA class I molecules located on the tumor cell surface binds to the surface HLA class I molecules. Additionally or alternatively, the agent that interacts with MHC $\beta_2$-microglobulin HLA class I molecules located on the tumor cell surface reduces the number of the surface HLA class I molecules. Additionally or alternatively, the agent that interacts with MHC $\beta_2$-microglobulin HLA class I molecules located on the tumor cell surface stimulates apoptosis in the cells, wherein apoptosis is defined as intracellular changes leading to cell death.

An agent that interacts with MHC $\beta_2$-microglobulin HLA class I molecules may comprise a protein, such as $\beta_2$-microglobulin, a polypeptide, such as a fragment of $\beta_2$-microglobulin, or a functional equivalent thereof comprising conservative substitutions, wherein conservative substitutions are those substitutions which do not significantly effect the structure or function of the protein or polypeptide. Also, the polypeptide may be a non-natural polypeptide which has chirality not found in nature, i.e., D-amino acids in place of L-amino acids.

Alternatively, the agent that interacts with MHC $\beta_2$-microglobulin HLA class I molecules may comprise a peptidomimetic, wherein the compound has a bond, a peptide backbone or an amino acid component replaced with a suitable mimic. Examples of unnatural amino acids which may be suitable amino acid mimics include ($\beta$-alanine, L-$\alpha$-amino butyric acid, L-aspartic acid, L-glutamic acid, N-$\epsilon$-Boc-N-$\alpha$-CBZ-L-lysine, L-norleucine, L-norvaline, Boc-p-nitro-L-phenylalanine, Boc-hydroxyproline, and the like.

In another embodiment, the agent that interacts with MHC $\beta_2$-microglobulin HLA class I molecules is an antibody. In one embodiment, the antibody is a monoclonal antibody. The monoclonal antibody may be human, humanized, primatized, or a chimeric antibody. In yet another embodiment, the agent is a fragment of an antibody. For example, the agent that interacts with MHC $\beta_2$-microglobulin HLA class I molecules may comprise a Fab fragment of an anti-$\beta_2$m antibody. Preferably, the Fab fragment is a F(ab')Z fragment. In an embodiment, the agent comprises the variable domain of an anti-$\beta_2$m antibody. In an embodiment, the antibody is an IgG antibody.

The present invention also describes reduction of tumor growth or proliferation by application of a composition comprising an agent that binds to $\beta_2$-microglobulin located on the tumor cell surface. An agent that binds to $\beta_2$-microglobulin may comprise a protein, a polypeptide or peptide fragment, or a functional equivalent thereof comprising conservative substitutions, wherein conservative substitutions are those substitutions which do not significantly effect the structure or function of the polypeptide or peptide. Also, the polypeptide may be a non-natural polypeptide which has chirality not found in nature, i.e., D-amino acids in place of L-amino acids.

Alternatively, the agent binds to $\beta_2$-microglobulin may comprise a peptidomimetic, wherein the compound has a bond, a peptide backbone or an amino acid component replaced with a suitable mimic. Examples of unnatural amino acids which may be suitable amino acid mimics include ($\beta$-alanine, L-$\alpha$-amino butyric acid, L-aspartic acid, L-glutamic acid, N-$\epsilon$-Boc-N-$\alpha$-CBZ-L-lysine, L-norleucine, L-norvaline, Boc-p-nitro-L-phenylalanine, Boc-hydroxyproline, and the like.

In another embodiment, the agent that binds to $\beta_2$-microglobulin is an antibody. In one embodiment, the antibody is a monoclonal antibody. The monoclonal antibody may be human, humanized, primatized, or a chimeric antibody. In yet another embodiment, the agent is a fragment of an antibody. For example, the agent binds to $\beta_2$-microglobulin may comprise an Fab fragment of an anti-$\beta_2$m antibody. Preferably, the Fab fragment is a F(ab')Z fragment. In an embodiment, the agent comprises the variable domain of an anti-$\beta_2$m antibody. In an embodiment, the antibody is an IgG antibody.

$\beta_2$-Microglobulin as a Negative Growth Regulator of Tumor Cells

Multiple myeloma (MM) is a B-cell neoplasm characterized by the accumulation of malignant plasma cells in the bone marrow. The level of $\beta_2$-microglobulin ($\beta_2$m) is one of the most important independent prognostic factors in multiple myeloma, yielding a reliable prediction of survival (Bataille, R., et al., *Blood,* 63:468-476, 1984; Cuzick, J., et al., *Br. J. Cancer,* 52:1-6, 1985). These data attest to an important yet unidentified role of $\beta_2$m in MM. In vitro studies show that primary myeloma cells (Bataille, R., et al., *Cancer Invest.,* 6:271-277, 1988) and myeloma cell lines (Brenning, G., et al., *Scand. J. Haematol.,* 37:280-288, 1986) produce high levels of $\beta_2$m. Thus, it is presumed that myeloma cells contribute to high levels of serum $\beta_2$m, which hence has been considered an indicator of tumor burden.

The MHC class I molecule, present on the surface of most nucleate cells, forms a trimolecular complex consisting of $\beta_2$m, an a chain, and an antigenic peptide. In the thymus, the class I $\alpha$-chain-$\beta_2$m complex affects the generation of a CD8$^+$ cytotoxic T lymphocyte (CTL) repertoire (Blackman, M., et al., *Science,* 248:1335-1341, 1990). In the periphery, the function of the class I $\alpha$-chain-$\beta_2$m complex is to present antigens, in the form of peptides derived from degraded endogenously synthesized proteins, to CTLs (Townsend, A. R., and Bodmer, H., *Annu. Rev. Immunol.,* 7:601-624, 1989). The class I $\alpha$-chain-$\beta_2$m complex also affects the target-cell sensitivity of natural killer (NK) cells and may modify the NK cell repertoire (Ljubggren, H. G. and Karre, K., *Immunol. Today,* 11:237-244, 1990). MHC class I molecules also serve as important signal-transducing molecules involved in the regulation or fine-tuning of immune responses (Skov., S., J. *Tissue Antigens,* 51:215-223, 1998). Ligation of MHC class I molecules on T and B cells by mobilized antibodies triggers signal transduction, which is involved in responses ranging from anergy and apoptosis to cell proliferation and IL-2 production (Skov., S., J. *Tissue Antigens,* 51:215-223, 1998; Skov, S., et al., *J. Cell Biol.,* 139:1523-1531, 1997). These findings indicate that, in addition to antigen presentation, MHC class I molecules or their components play an important role in the regulation of immune responses.

$\beta_2$m is a 11.6-kDa non-glycosylated polypeptide composed of 100 amino acids. It is part of the major histocompatibility complex (MHC) class I molecules on the cell surface of all nucleate cells. Its best-characterized function is to interact with and stabilize the tertiary structure of the MHC class I $\alpha$-chain (Bjorkman, P. J., and Parham, P., *Ann. Rev. Biochem.,* 59:253-288, 1990). Because it is non-covalently associated with the $\alpha$-chain and has no direct attachment to the cell membrane, $\beta_2$m on the cell surface can exchange with free $\beta_2$m present in serum-containing medium (Hyafil, F., and Strominger, J. L., *Proc. Natl. Acad. Sci. U.S.A.,* 76:5834-5838, 1979; Parker, K. C., and Strominger, J. L., *Biochemistry,* 24:5543-5550, 1985).

As a result of shedding from cell surfaces or intracellular release, free $\beta_2$m is found in body fluids under physiological conditions. $\beta_2$m is almost exclusively catabolized within the kidney; at least 95%, and possibly 100%, of circulating $\beta_2$m is eliminated via glomerular filtration (Karlsson, F. A., et al., *Scand. J. Clin. Lab. Invest.,* 40:S27-S37, 1980). In normal individuals, the serum concentration of $\beta_2$m is usually <2 mg/L and the urinary excretion <400 µg/24 hours (Revillard, J. P., and Vincent, C., *Contrib. Nephrol.,* 62:44-53, 1988; Schardijn, G. H., and Statius van Eps, L. W., *Kidney Int.,* 32:635-641, 1987).

Increased synthesis and release of $\beta_2$m, as indicated by an elevated serum $\beta_2$m concentration, occur in autoimmune and infectious diseases (Revillard, J. P., et al., *Eur. J. Rheumatol. Inflamm.,* 5:398-405, 1982; Walters, M. T., et al., *Ann. Rheum. Dis.,* 48:905-911, 1989; Grieco, M. H., et al., *Clin. Immunol. Immunopathol.,* 32:174-184, 1984; Lifson, A. R., et al., *Lancet,* 339:1436-1440, 1992) and in malignancies (Campos, L., et al., *Blut,* 48:221-226, 1984; Bunning, R. A., et al., *J. Urol.,* 121:624-625, 1979), including MM (Barlogie, B., et al., *Blood,* 93:55-65, 1999; Bataille, R., et al., *Blood,* 63:468-476, 1984). Thus, both T- and B-cell antigen stimulation increases cellular $\beta_2$m release by cells (Sprague, S. M. and Popovtzer, M. M., Kidney Int., 47:1-6, 1995). In vitro and in vivo studies demonstrate that the synthesis and release of $\beta_2$m are mediated by various cytokines. Tumor necrosis factor (TNF)-$\alpha$, IL-2, and both interferon (IFN)-$\alpha$ and -$\gamma$ stimulate the synthesis and release of $\beta_2$m from various cell types in culture (Sprague, S. M. and Popovtzer, M. M., *Kidney Int.,* 47:1-6, 1995). In vivo application of TNF-$\alpha$, IFN-$\alpha$, or IFN-$\gamma$ increases serum $\beta_2$m concentrations (Sprague, S. M. and Popovtzer, M. M., *Kidney Int.,* 47:1-6, 1995).

In MM and other malignancies, such as leukemias and lymphomas (Campos, L., et al., *Blut,* 48:221-2261, 1984; Bunning, R. A., et al., *J. Urol.,* 121:624-625, 1979; Bataille, R., et al., *Blood,* 63:468-476, 1984; Cuzick, J., et al., *Br. J. Cancer,* 52:1-6, 1985), elevated serum levels of $\beta_2$m are present and correlate with a poor patient outcome. For example, in vitro studies have shown that primary myeloma cells and myeloma cell lines produce $\beta_2$m (Bataille, R., et al., *Cancer Invest.,* 6:271-277, 1988; Brenning, G., et al., *Scand. J. Haematol.,* 37:280-288, 1986). Thus, it is presumed that myeloma cells contribute to the high levels of serum $\beta_2$m, which has therefore been considered a surrogate marker for tumor burden in myeloma patients. According to data collected from >1,000 myeloma patients at U. of Arkansas Myeloma Institute for Research and Therapy (MIRT), serum $\beta_2$m can be as high as 80 mg/L. The concentrations of $\beta_2$m in tumor sites, such as bone marrow, may be even higher.

Figure 2:
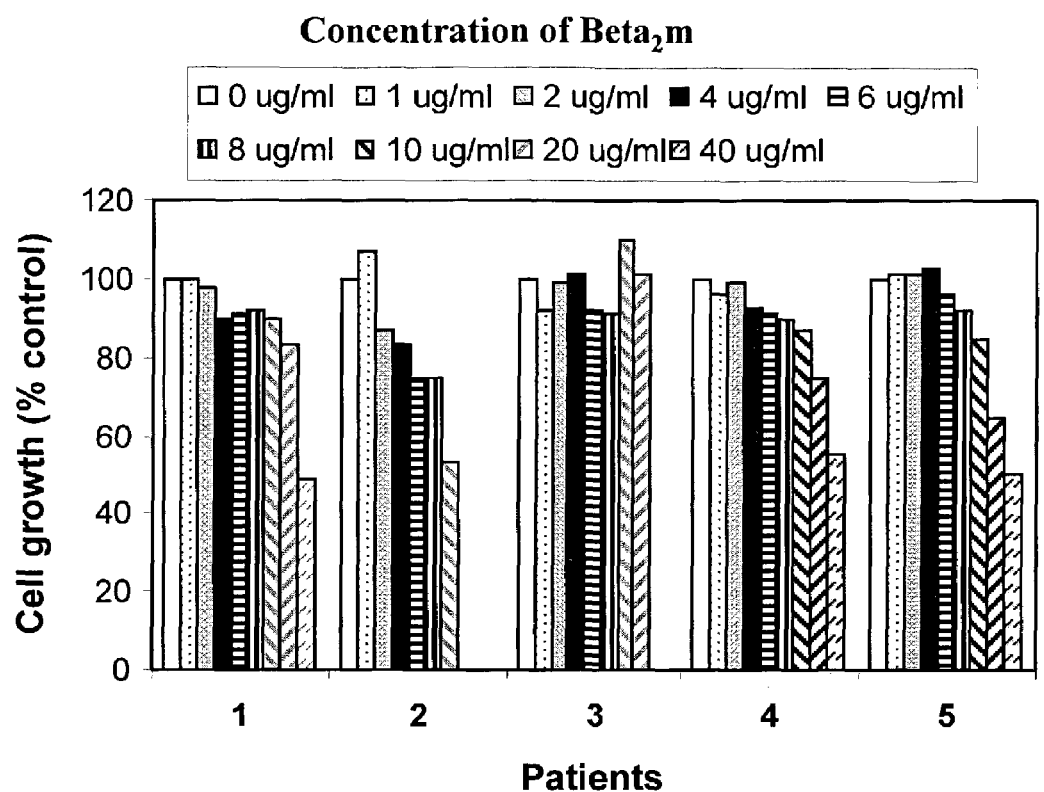
FIG. 2. illustrates the proliferation of primary myeloma cells from 5 patients in response to different concentrations of $\beta_2$m in accordance with an embodiment of the present invention wherein $^3$H-thymidine incorporation assay was performed in a 24-hour culture and cell growth is expressed as a percentage of control.

In an embodiment, the present invention recognizes that $\beta_2$m suppresses the growth and proliferation of myeloma cells. As shown in FIG. 1, the proliferation of four myeloma cell lines (ARK-RS, ARP-1, RPMI-8226, and U266) is suppressed by $\beta_2$m in a dose and time dependent manner. The anti-proliferative effects of $\beta_2$m are seen in Epstein Barr Virus negative (EBV$^-$) cells (FIGS. 1A and 1B), as well as Epstein Barr Virus positive (EBV$^+$) cells (FIG. 1C), as well as in a majority of primary myeloma cells isolated from patients (FIG. 2). For example, as shown in FIG. 2, $\beta_2$m inhibits the proliferation of myeloma cells isolated from four out of five myeloma patients in a dose-dependent manner.

Figure 3:
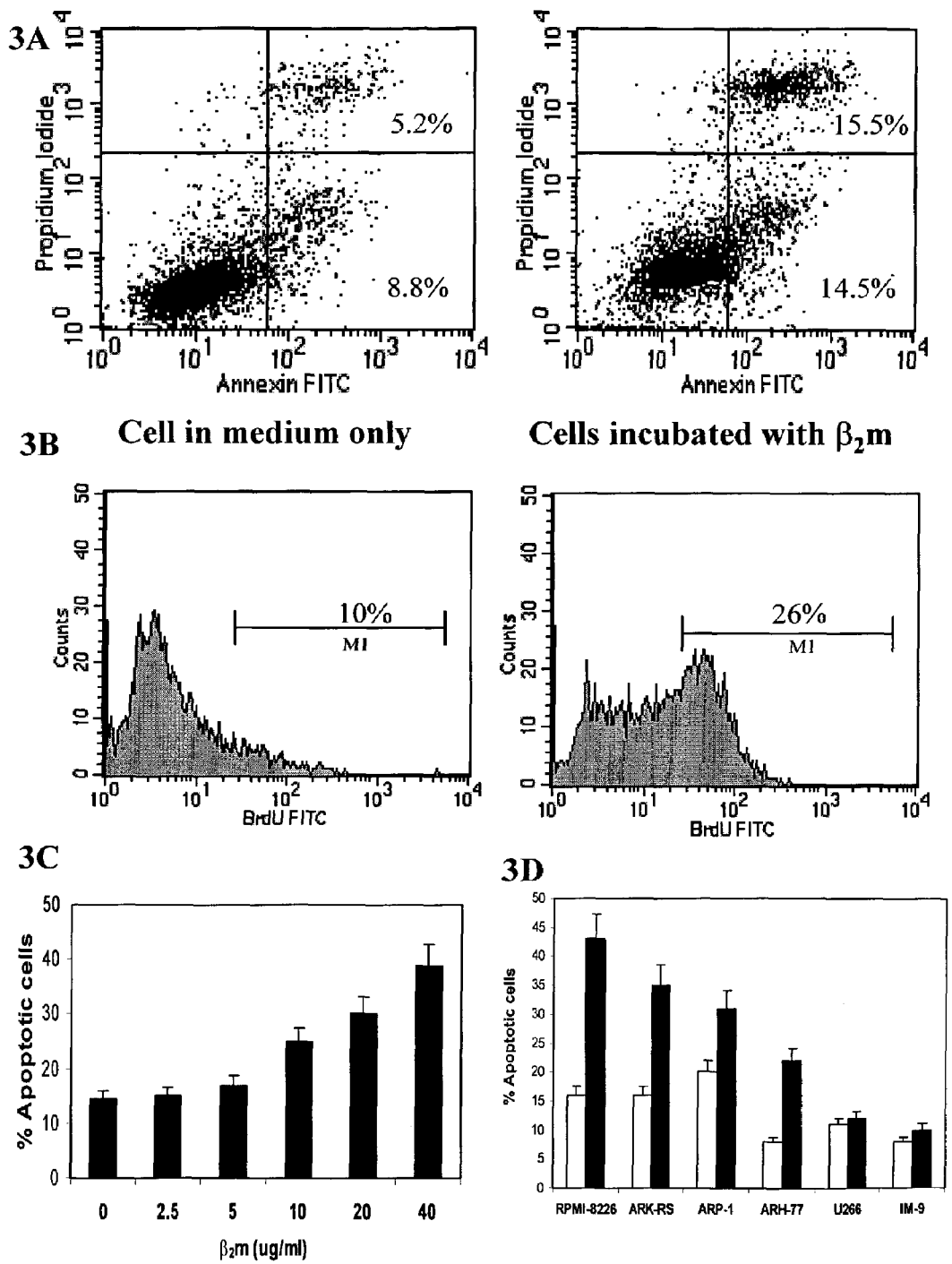
FIG. 3 illustrates $\beta_2$m-induced apoptosis in myeloma cells in accordance with an embodiment of the present invention wherein (A) shows representative dot plots showing apoptotic RPMI-8226 cells determined by propidium idodide (PI) and Annexin V staining; (B) shows representative histograms showing apoptotic RPMI-8226 cells determined by TUNEL assay using $\beta_2$m at 40 µg/ml, where the percentage of apoptotic cells is indicated by the horizontal bar; (C) shows dose-dependent induction of apoptosis in RPMI-8226 myeloma cells by $\beta_2$m; and (D) shows $\beta_2$m-induced apoptosis in six myeloma cell-lines (□, control cells; ■, cells treated with 40 µg/ml $\beta_2$m). Values are expressed as the mean ±SD of 5 experiments.

In addition to growth inhibition, $\beta_2$-microglobulin may induce apoptosis in myeloma cells. Thus, addition of $\beta_2$m leads to significant apoptosis in myeloma cell lines and primary tumor cells (FIG. 3). Preferably, induction is dose-dependent, with substantial apoptosis induced by doses which provide a concentration of $\beta_2$m at the cell surface of about 40 µg/ml (FIG. 3).

Apoptosis is a self-destructive process characterized by nuclear and cytoplasmic condensation, DNA fragmentation, dilation of the endoplasmic reticulum, and alterations in cell membrane composition (Bratton, S. B., et al., *Exp. Cell. Res.,* 256:27-33, 2000). In mammalian cells, the onset of apoptosis usually correlates with the activation of a family of cysteine proteases called caspases. Caspases can activate one another and, consequently, can initiate specific caspase cascades. Caspase-8 and -9 appear to be the apical caspases activated in apoptosis induced by death receptors and mitochondrial stress, respectively. These caspases are responsible for activating various effector caspases, including caspases-3, -6, and -7, which contain short prodomains.

Figure 4:
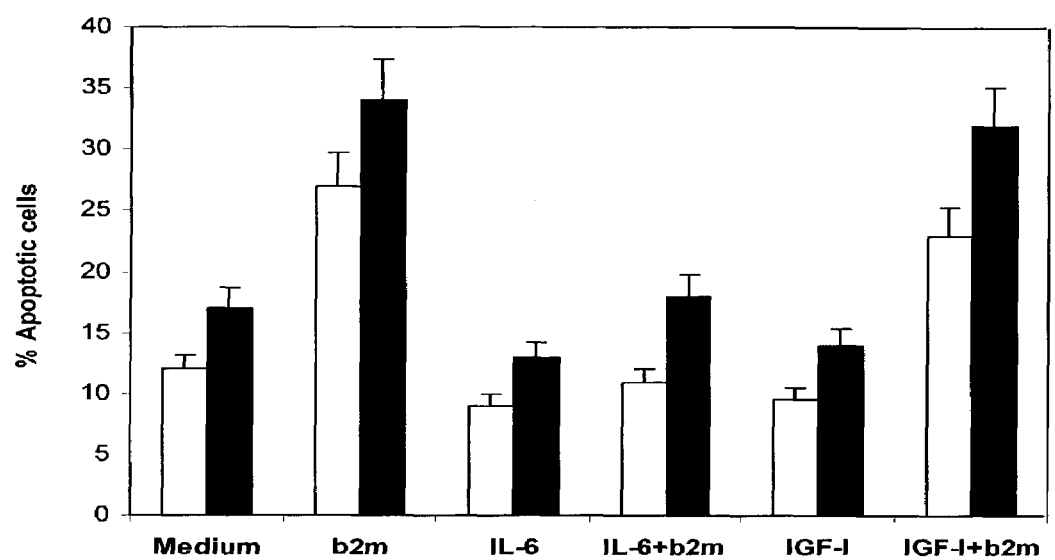
FIG. 4 illustrates that IL-6, but not IGF-I, inhibits $\beta_2$m-induced apoptosis in myeloma cells in accordance with an embodiment of the present invention. Shown are percentages of apoptotic cells among ARK-RS (□) and RPMI-8226 (■) myeloma cells. Values are expressed as the mean ±SD of 3 experiments.
Figure 5C:
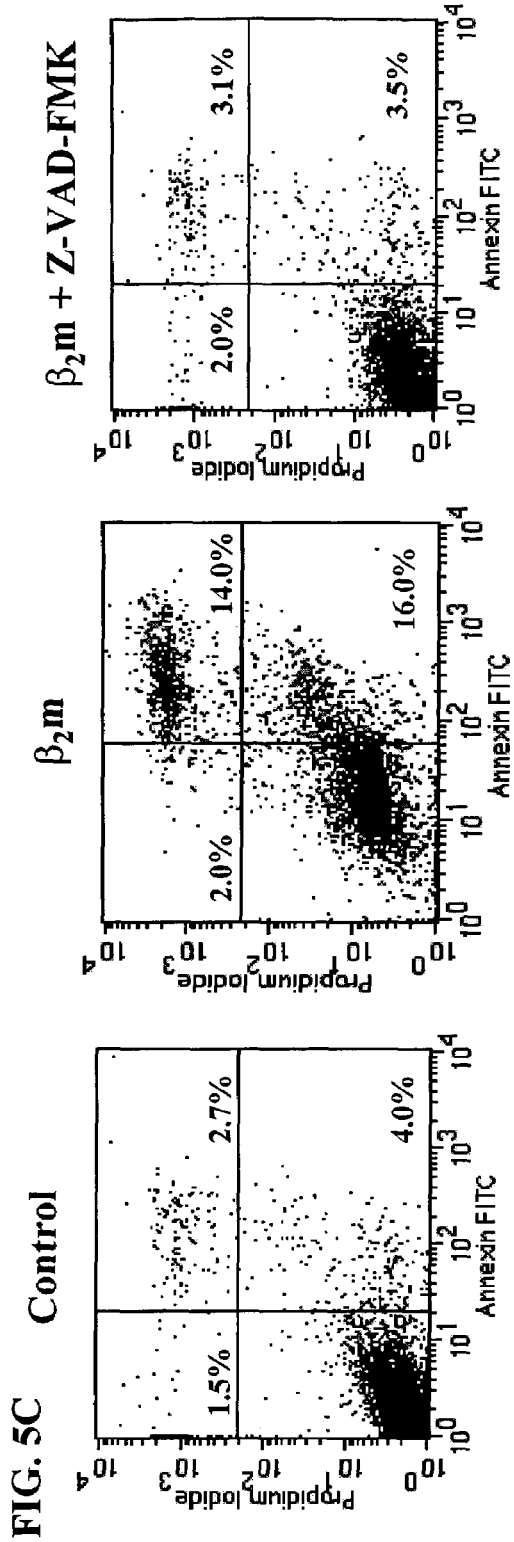
FIG. 5 illustrates that, in accordance with an embodiment of the present invention, $\beta_2$m-induced apoptosis in myeloma cells involves caspase activation wherein (A) shows western blot analysis showing $\beta_2$m-induced activation and processing of caspase-3 and cleavage of PARP in RPMI-8226, ARK-RS, and ARP-1 cells, but not U266 cells; (B) shows that the pan-caspase inhibitor Z-VAD-FMK inhibits $\beta_2$m-induced cleavage of PARP in ARK-RS and RPMI-8226 cells; (C) shows $\beta_2$m-induced apoptosis in RPMI-8226 cells ($\beta_2$m: 40 µg/ml in 48-hour culture); and (D) shows anti-Fas antibody-induced apoptosis in Jurkat cells (antibody: 100 ng/ml in 18-hour culture).
Figure 5D:
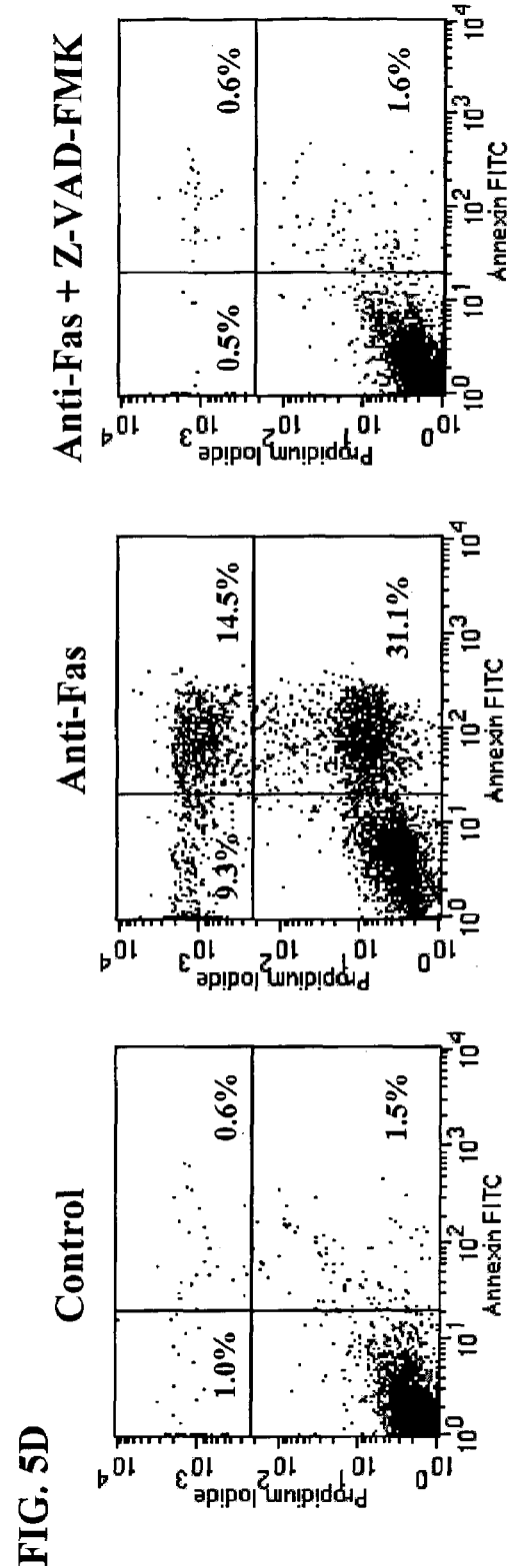

In an embodiment, the growth factor interleukin-6 (IL-6), but not insulin-like growth factor (IGF-1), prevents the apoptosis promoting effects of $\beta_2$m (FIG. 4). Also, and/or alternatively, the apoptosis promoting effects of $\beta_2$m are mediated at least in part by activation of caspases. As shown in FIG. 5, $\beta_2$m-induced apoptosis in myeloma cells involves activation and cleavage of caspase-3 and PARP (FIGS. 5A and B). Further, treatment of cells with the pan-caspase inhibitor Z-VAD-FMK inhibits induction of apoptosis and cleavage of PARP by $\beta_2$m (FIGS. 5B and 5C). This caspase inhibitor also abrogates apoptosis induced by the anti-Fas antibody 7C11 (IgM, Immunotech) in Jurkat cells (FIG. 5D). Thus, treatment of cells with $\beta_2$m results in activation of caspase-3 and cleavage of PARP in myeloma ARK-RS, ARP-1 and RPMI-8226 cells.

Figure 6:
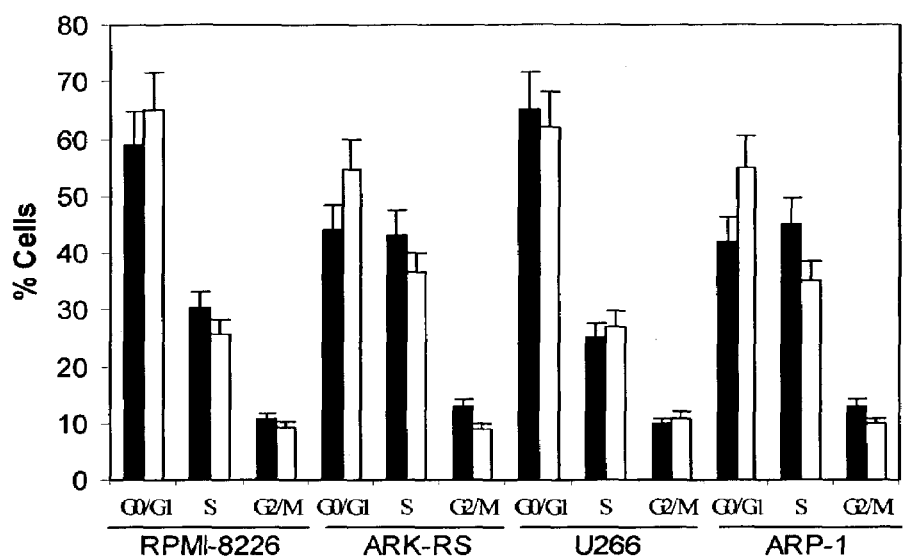
FIG. 6 illustrates (A) $\beta_2$m-induced changes in cell cycle distribution and (B) changes in cyclin expression in accordance with an embodiment of the present invention. Shown are the results of 4 myeloma cell lines (RPM1-8226, ARK-RS, U266, ARP-1) in response to 20 µg/ml $\beta_2$m (■—control cells; □—$\beta_2$m-treated cells). Values in (A) are expressed as the mean ±SD of 3 experiments.
Figure 6:
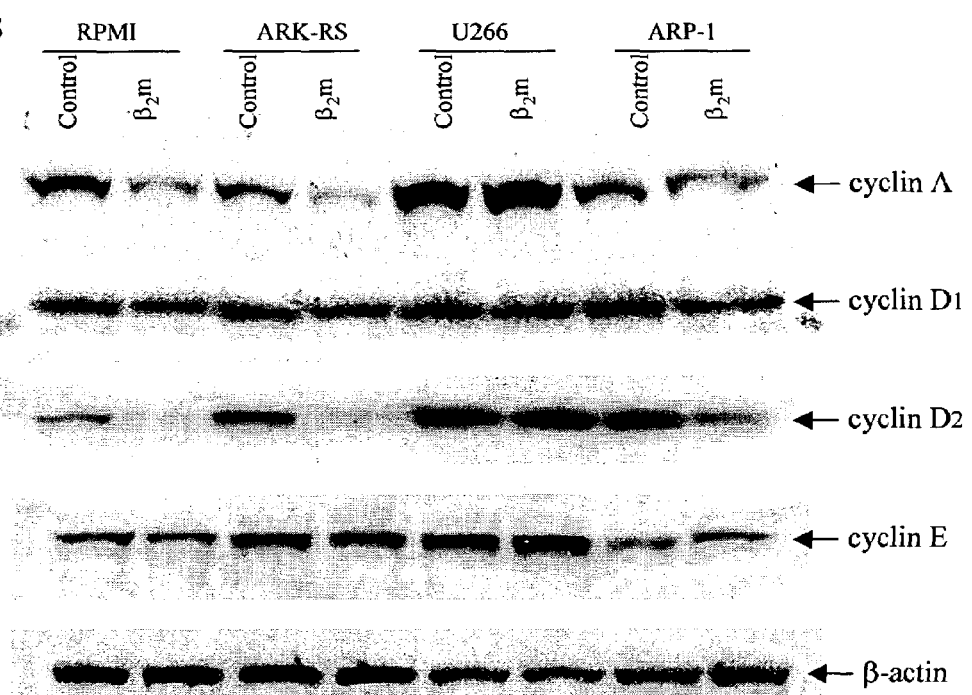

There may be more than one pathway by which $\beta_2$m acts on cancer cells. In an embodiment, $\beta_2$m arrests the progression of tumor cells through the cell cycle. For example, in an embodiment, treatment of tumor cells with $\beta_2$m causes an alteration in cell cycle distribution. Thus, in an embodiment, treatment of tumor cells with $\beta_2$m results in growth arrest in $G_0/G_1$. Thus, treatment of tumor cells with $\beta_2$m may result in an increased percentage of cells in the $G_0/G_1$ phases of the cell cycle and a decreased percentage in S and $G_2$/M phases (FIG. 6A). Alternatively and/or additionally, treatment of tumor cells with $\beta_2$m down-regulates cyclins A and D2 (FIG. 6B).

Agents That Bind $\beta_2$-Microglobulin Inhibit Cancer Cell Growth and Proliferation The present invention recognizes that $\beta_2$m plays an important role in the regulation of tumor cell growth and proliferation. Interestingly, antibodies to $\beta_2$m do not prevent $\beta_2$m-mediated inhibition of cell growth and proliferation, but also inhibit growth and proliferation of tumor cells. This is in contrast to prior descriptions of the use of $\beta_2$m as an anti-cancer therapeutic (Mori, M., et al., *Blood,* 94:2744-2753, 1999; Mori, M., *Cancer Res.,* 61:4414-4417, 2001) where anti-$\beta_2$m antibodies were found to prevent the apoptotic effects of $\beta_2$m (Mori, M., et al., *Blood,* 94:2744-2753, 1999).

Thus, in one aspect, the present invention comprises a composition for the treatment of cancer growth or proliferation comprising a pharmacologically effective amount of an agent that binds to $\beta_2$-microglobulin in a pharmaceutically acceptable carrier, wherein a pharmacologically effective amount of the $\beta_2$-microglobulin binding agent comprises sufficient agent to reduce growth and proliferation of the cancer.

Figure 7:
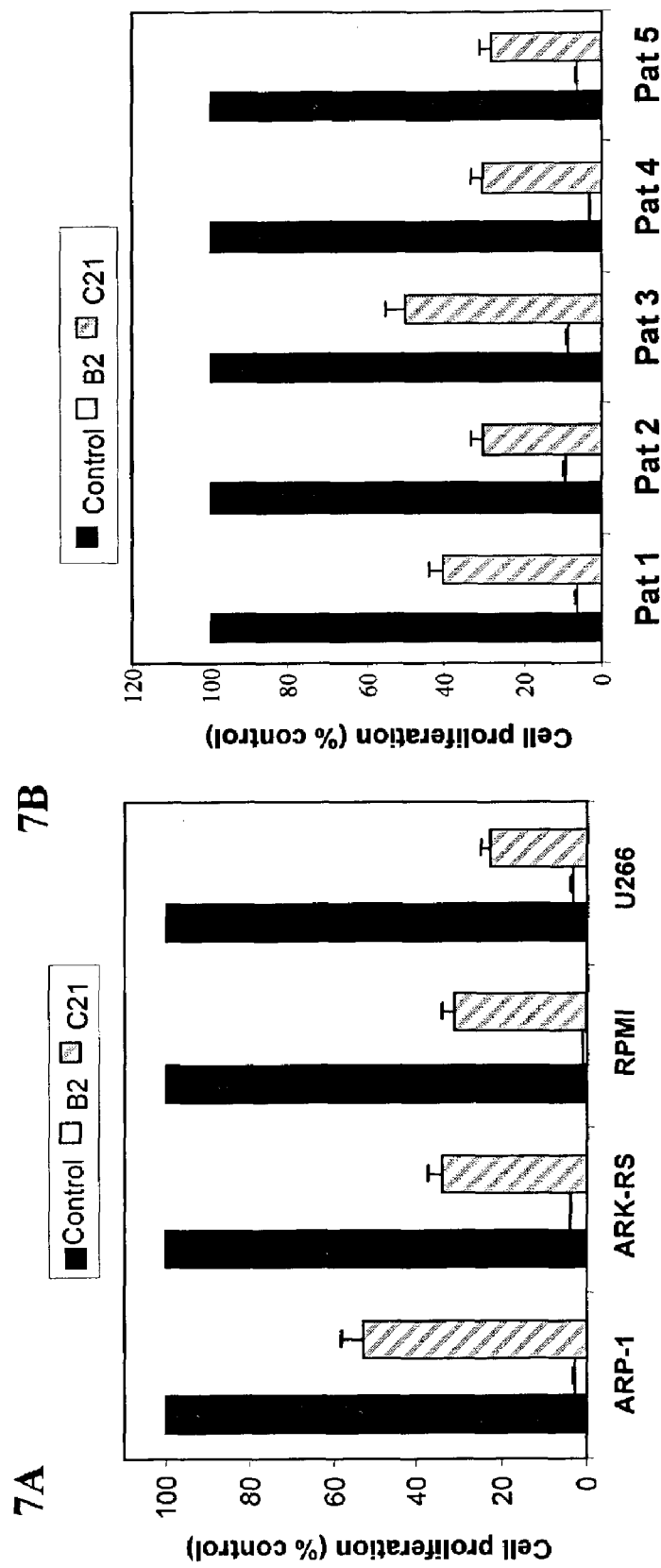
FIG. 7 illustrates that anti-$\beta_2$m antibodies (B2 and C21) inhibit the proliferation of (A) established myeloma cell lines (ARP-1, ARK-RS, RPM1, and U266) and (B) primary myeloma cells in accordance with an embodiment of the present invention.

Thus, in an embodiment, $\beta_2$m binding agents may suppress tumor cell growth and proliferation. For example, addition of anti-$\beta_2$m antibodies to myeloma cell cultures suppresses the growth and proliferation of established myeloma cell lines (FIG. 7A) and primary myeloma cells from patients (FIG. 7B). In an embodiment, the antibody reduces proliferation of the cancer by over 50%. More preferably, the antibody reduces proliferation of the cancer by over 75%, and even more preferably, by the antibody reduces proliferation of the cancer over 90%.

Figure 8A:
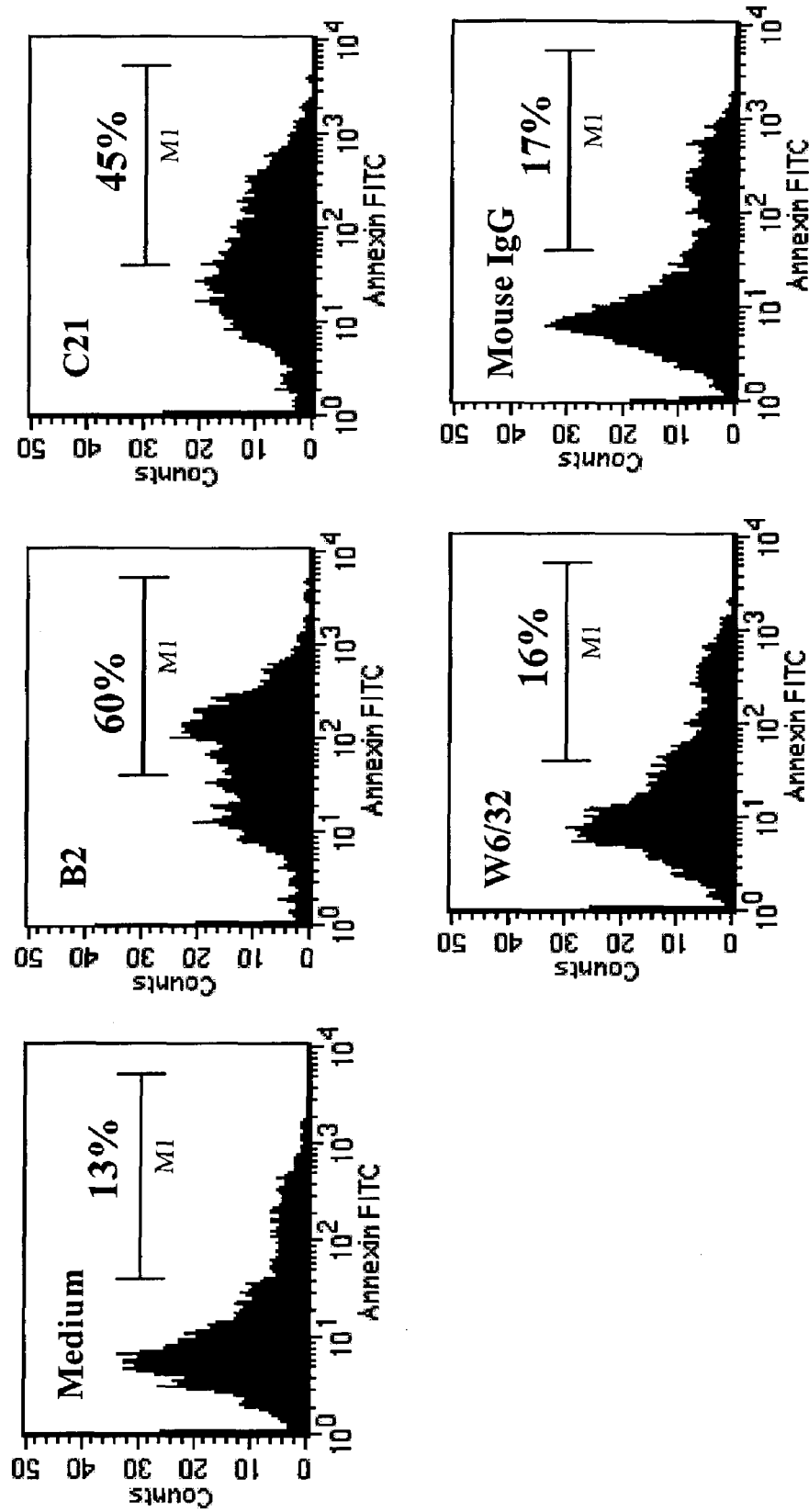
FIG. 8 illustrates that anti-$\beta_2$m antibodies (B2 and C21) induced apoptosis in myeloma cells (RPMI-8226) in accordance with an embodiment of the present invention wherein (A) shows the percentage increase in apoptotic cells (% apoptotic cells in population is indicated by horizontal bar) upon exposure of RPMI-8226 myeloma cells to anti-$\beta_2$m antibodies (B2 and C21), and (B) shows that anti-$\beta_2$m antibodies B2 and C21 did not block $\beta_2$m-induced apoptosis in myeloma cell lines ARK-RS (■) and RPMI-8226 (□) but induced apoptosis in the tumor cells, wherein control antibody W6/32 had no effect.
Figure 8B:
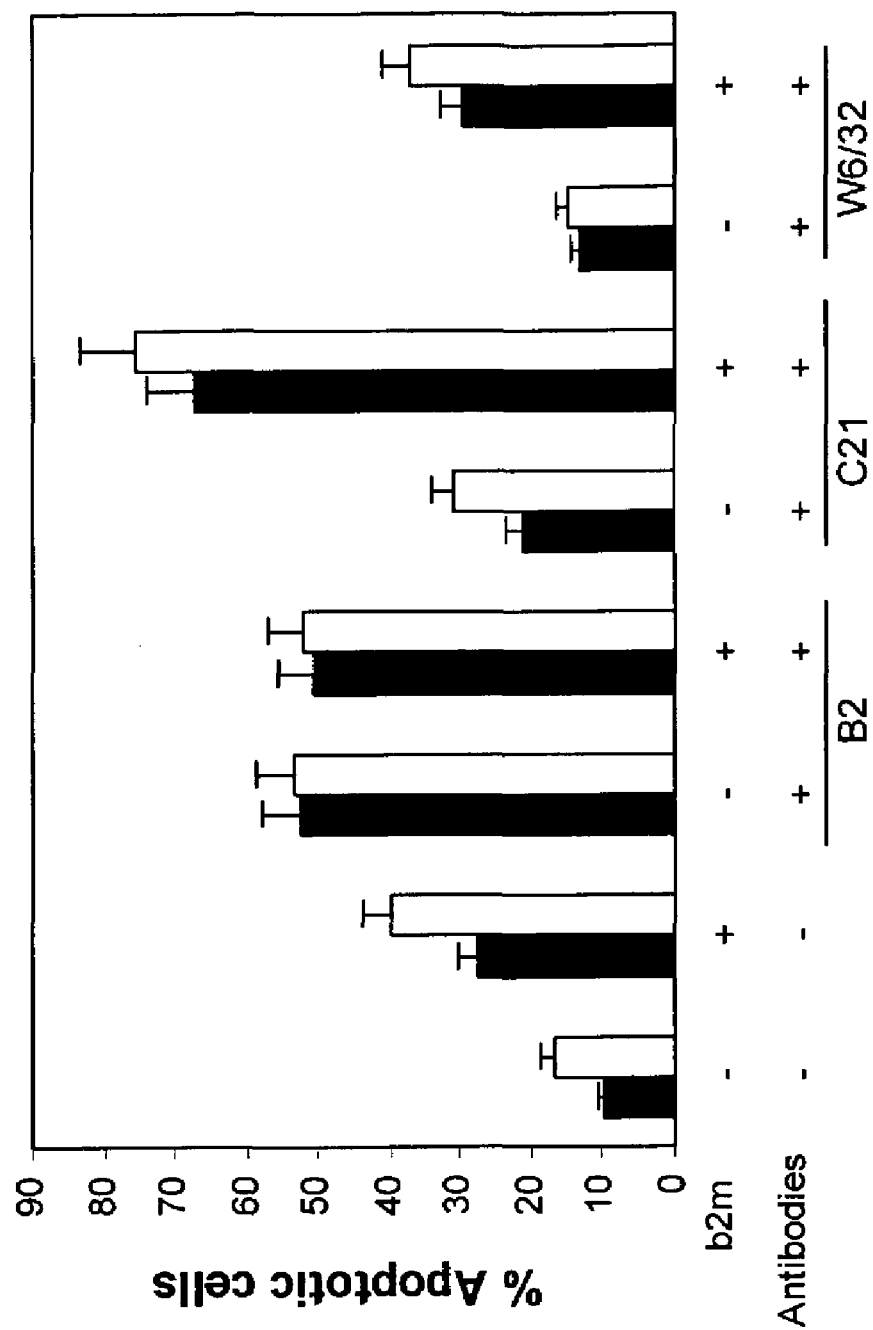

In an embodiment, anti-$\beta_2$-microglobulin antibodies induce apoptosis (FIG. 8A). Preferably, the apoptotic effects of anti-$\beta_2$-microglobulin binding agents are not inhibited by $\beta_2$m. In an embodiment, the effect of the antibody and $\beta_2$m is synergistic. For example, antibody C21 displays a stronger apoptosis inducing effect when used with $\beta_2$m than when used alone (FIG. 8B).

Preferably, the apoptotic inducing effects of anti-$\beta_2$-microglobulin binding agents are seen in a large variety of cell types. For example, U266 and IM-9 cells, which are less responsive to $\beta_2$m, are also sensitive to anti-$\beta_2$m antibody-induced apoptosis (data not shown). Thus, in an embodiment, tumors which are sensitive to the apoptotic effects of anti-$\beta_2$-microglobulin binding agents include myeloma tumor cells as well as lymphoma, leukemia and solid tumors including, but not limited to, breast cancer, melanoma, and colon cancer.

Figure 9:
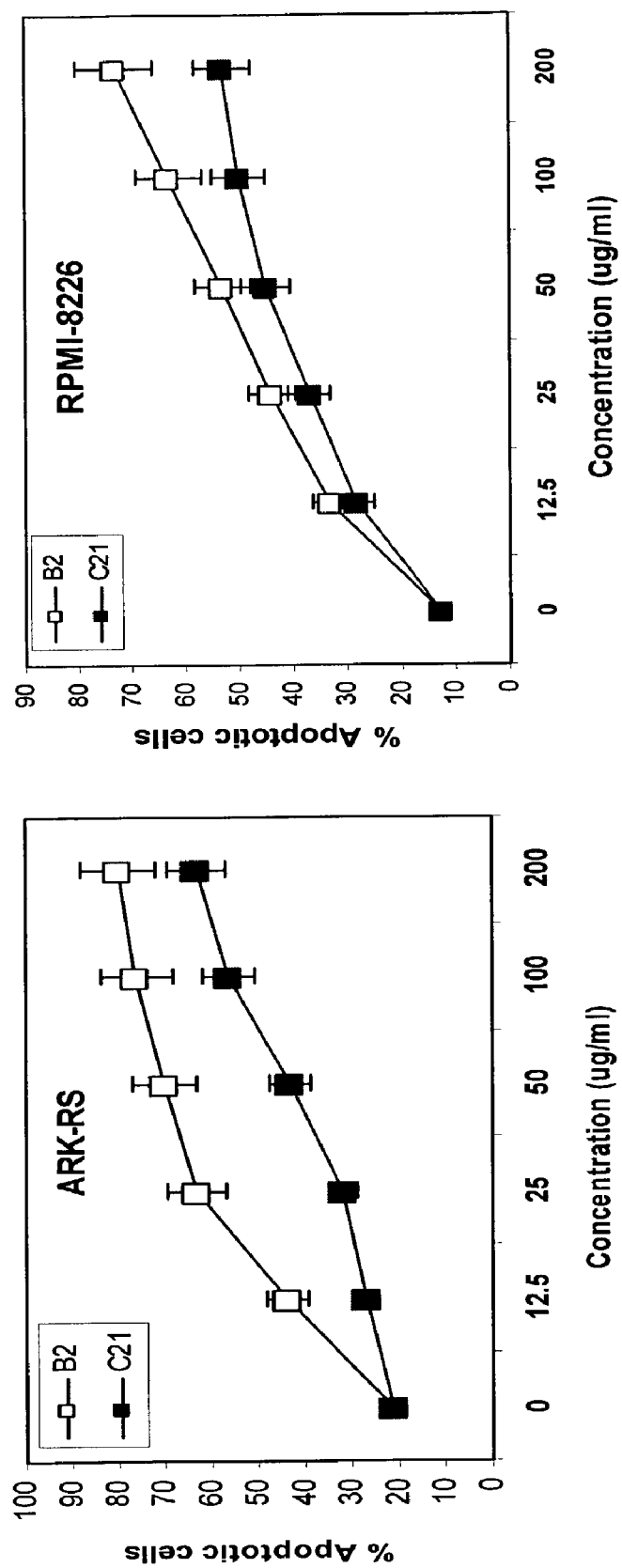
FIG. 9 illustrates induction of apoptosis in myeloma cell lines (ARK-RS and RPMI-8226) by increasing concentrations of anti-$\beta_2$m antibodies B2 and C21, as detected by Annexin-V and propidium iodide (PI) staining in accordance with an embodiment of the present invention.
Figure 10:
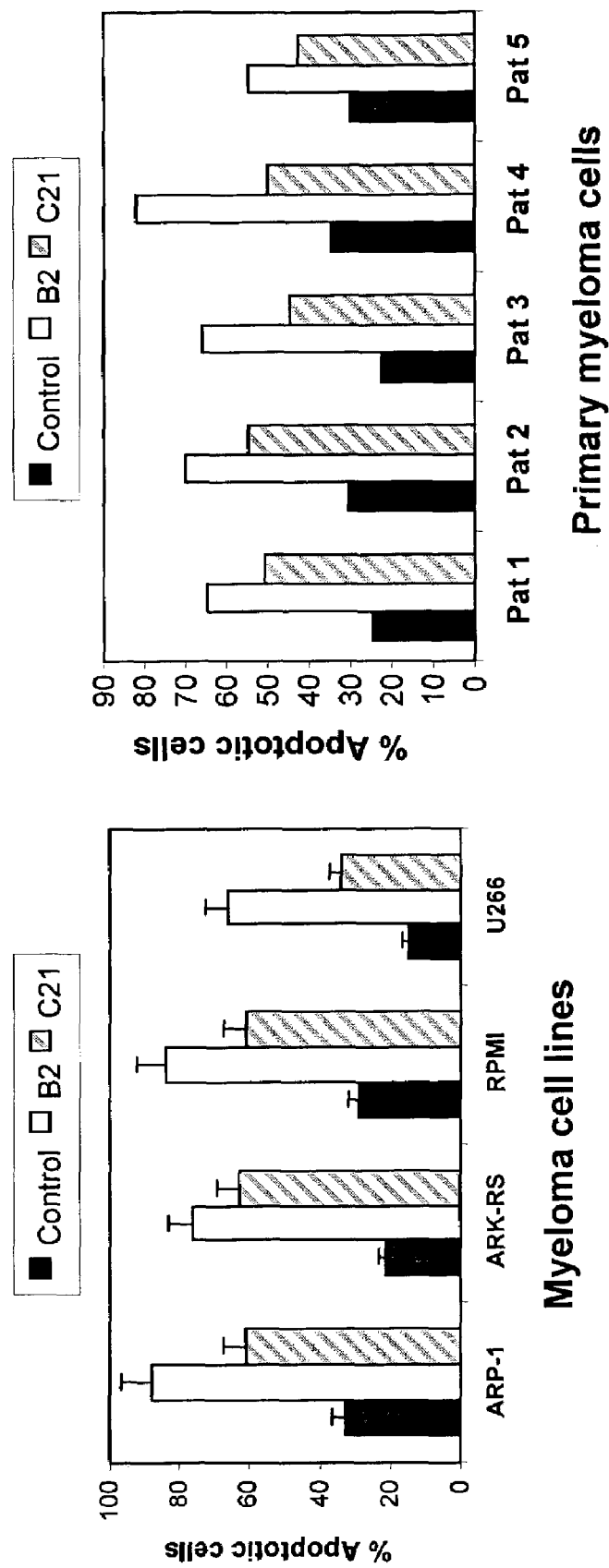
FIG. 10 illustrates that anti-$\beta_2$m antibodies (B2 and C21) induce apoptosis in myeloma cell lines (ARP-1, ARK-RS, RPMI, and U266) and primary myeloma cells isolated from 5 different patients (Pats. 1-5) in accordance with an embodiment of the present invention.

In an embodiment, agents that bind $\beta_2$m inhibit cell growth and proliferation by induction of apoptosis. Thus, in an embodiment, anti-$\beta_2$m antibodies induce apoptosis in a large percentage of myeloma cells (FIG. 8) in a dose-dependent (FIG. 9) and time-dependent (not shown) manner. The apoptosis-inducing effects of anti-$\beta_2$m antibodies are seen in both myeloma cell lines as well as primary tumor cells isolated from patients (FIG. 10). Also, the apoptosis-inducing effect is not restricted to B2 and C21 anti-$\beta_2$m antibodies, as similar results are obtained with other anti-$\beta_2$m antibodies (data not shown).

In an embodiment, there is a preferred range of $\beta_2$m binding agent concentrations. For example, in an embodiment, the agent comprises anti-$\beta_2$m antibody. Preferably, a pharmacologically effective amount of the antibody comprises a concentration at the tumor cell of 0.5 to 5,000 µg/ml. More preferably, a pharmacologically effective amount of the antibody comprises a concentration at the tumor cell of 5 to 500 µg/ml. Even more preferably, a pharmacologically effective amount of the antibody comprises a concentration at the tumor cell of 12.5 to 200 µg/ml (FIG. 9).

Figure 11:
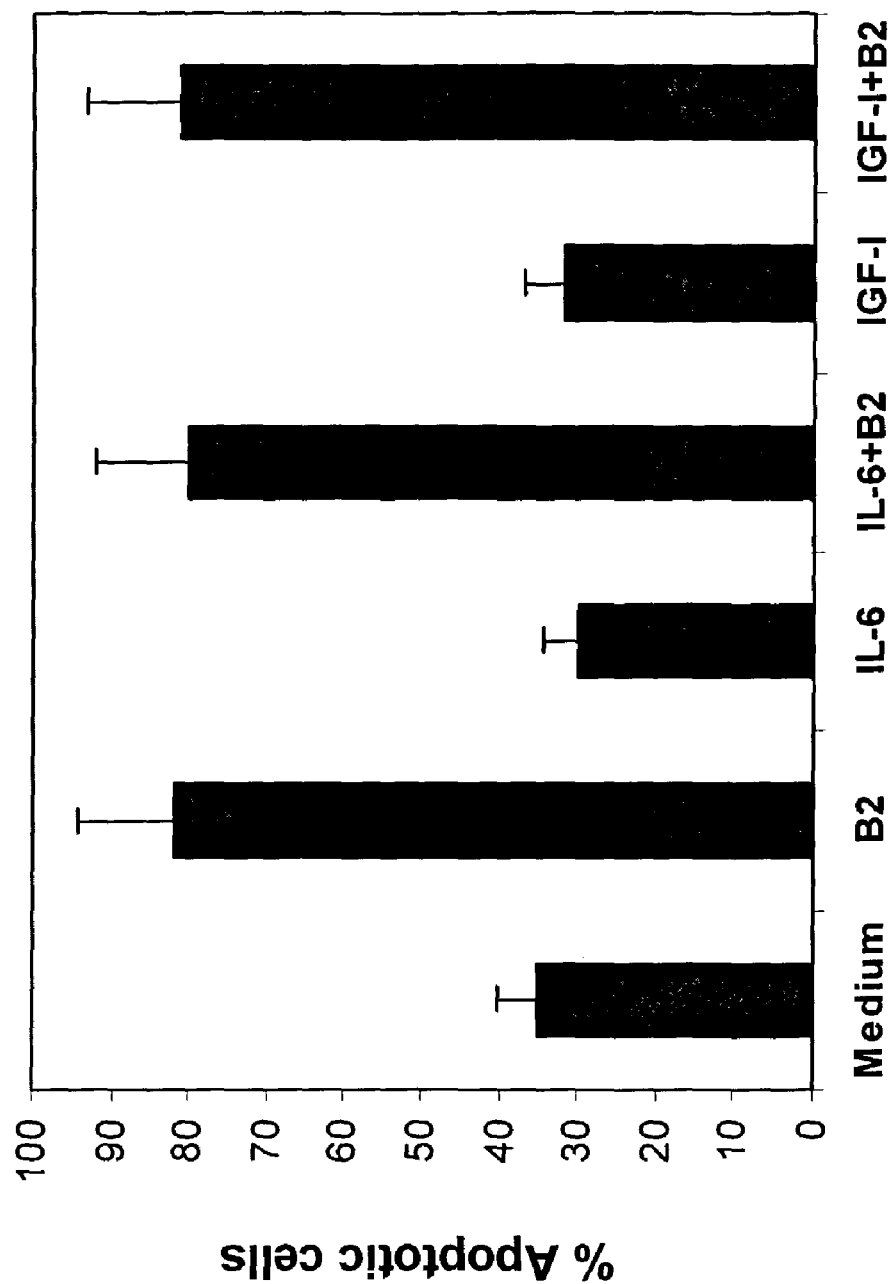
FIG. 11 illustrates that IL-6 and IGF-1 do not protect myeloma cells from B2 anti-$\beta_2$m antibody-induced apoptosis in accordance with an embodiment of the present invention.

Preferably, the apoptotic effects of $\beta_2$m binding agents are not counteracted by growth factors commonly upregulated in cancer. For example, IL-6 and insulin-like growth factor (IGF-I) are growth and survival factors in myeloma cells (Kawano et al., *Nature*, 332:83-85, 1988; Harding et al., *Blood*, 84:3063-3070, 1994; Georgii-Hemming et al., *Blood*, 88:2250-2258, 1996). In an embodiment, IL-6 does not protect cells against the apoptotic effect of anti-$\beta_2$m antibodies (FIG. 11). Also, in an embodiment, IGF-I does not protect cells against the apoptotic effect of anti-$\beta_2$m antibodies (FIG. 11).

Figure 12:
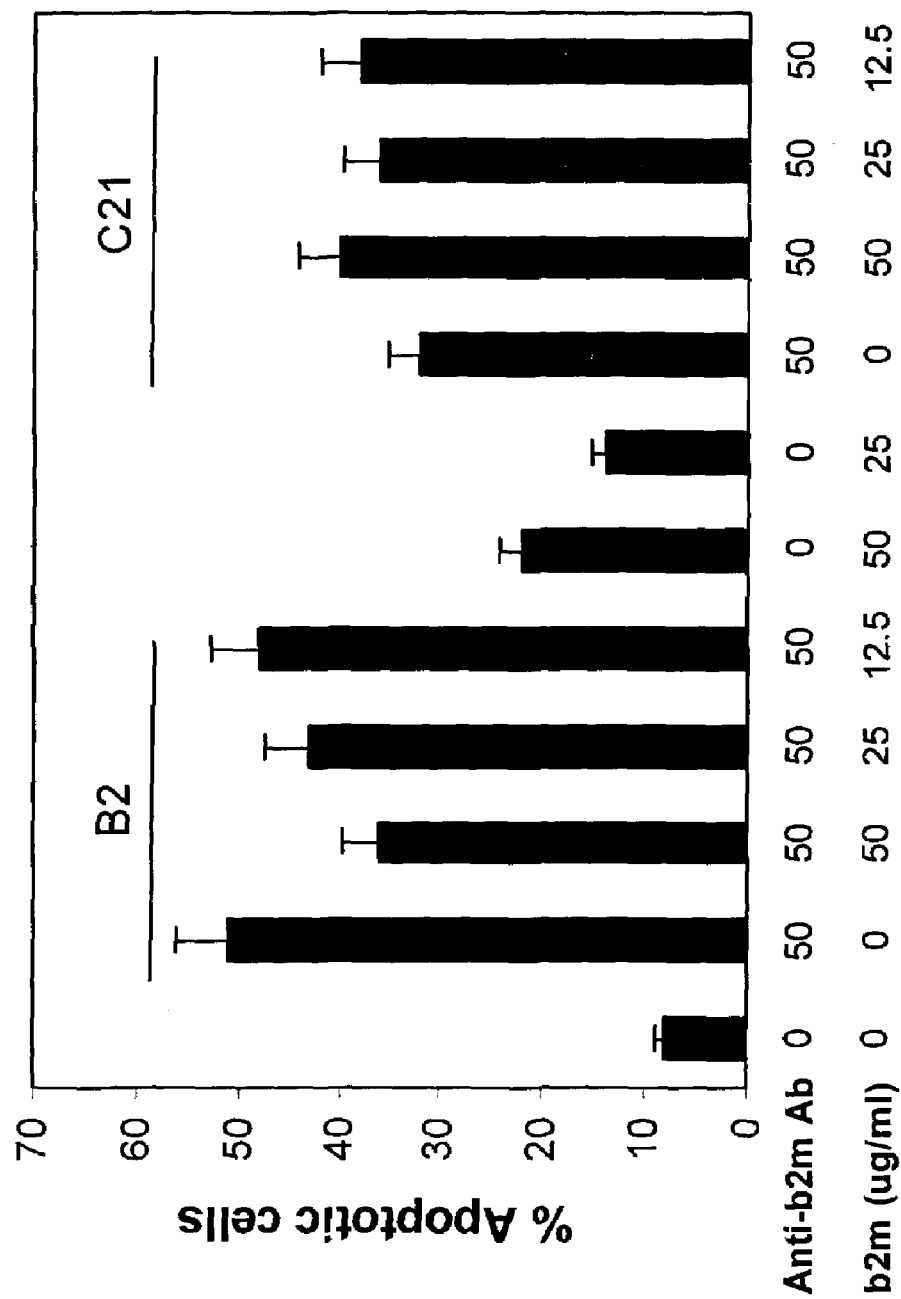
FIG. 12 illustrates that $\beta_2$m does not block the apoptotic effect of anti-$\beta_2$m antibody B2 and enhances apoptotic effects of C21 antibody on myeloma cells in accordance with an embodiment of the present invention.

In an embodiment, the apoptotic effects of agents that interact with $\beta_2$m is not inhibited or competed by endogenous $\beta_2$m. For example, as shown in FIG. 12, pre-incubation of anti-$\beta_2$m antibodies with a 50 to 12.5 fold excess molar concentration of $\beta_2$m does not inhibit apoptosis induced by C21 antibody, and inhibits apoptosis induced by B2 antibody only minimally. Also, in an embodiment, the apoptotic effect of $\beta_2$m binding agent is not inhibited by $\beta_2$m, but may be increased by $\beta_2$m. For example, the apoptosis-inducing effect of antibody C21 is actually enhanced by $\beta_2$m (FIGS. 8B and 12). Thus, in an embodiment, the presence of high concentrations of soluble $\beta_2$m in myeloma patients will not compromise the therapeutic potential of anti-$\beta_2$m antibodies.

A problem common to many chemotherapeutic protocols currently in use is that agents that are toxic to the tumor are also somewhat toxic to normal tissue. Thus, toxicity of anti-cancer agents may severely limit the usefulness of a treatment protocol. Preferably, the agents that interact with $\beta_2$m as chemotherapeutic agents are not toxic to normal hemapoietic cells. Thus, in an embodiment, normal blood lymphocytes comprising either resting or phytohemagglutinin-activated cells (FIG. 13), and purified bone marrow CD34+ cells from healthy individuals (FIG. 14) are resistant to the apoptotic effects of anti-$\beta_2$-m antibodies.

Figure 15:
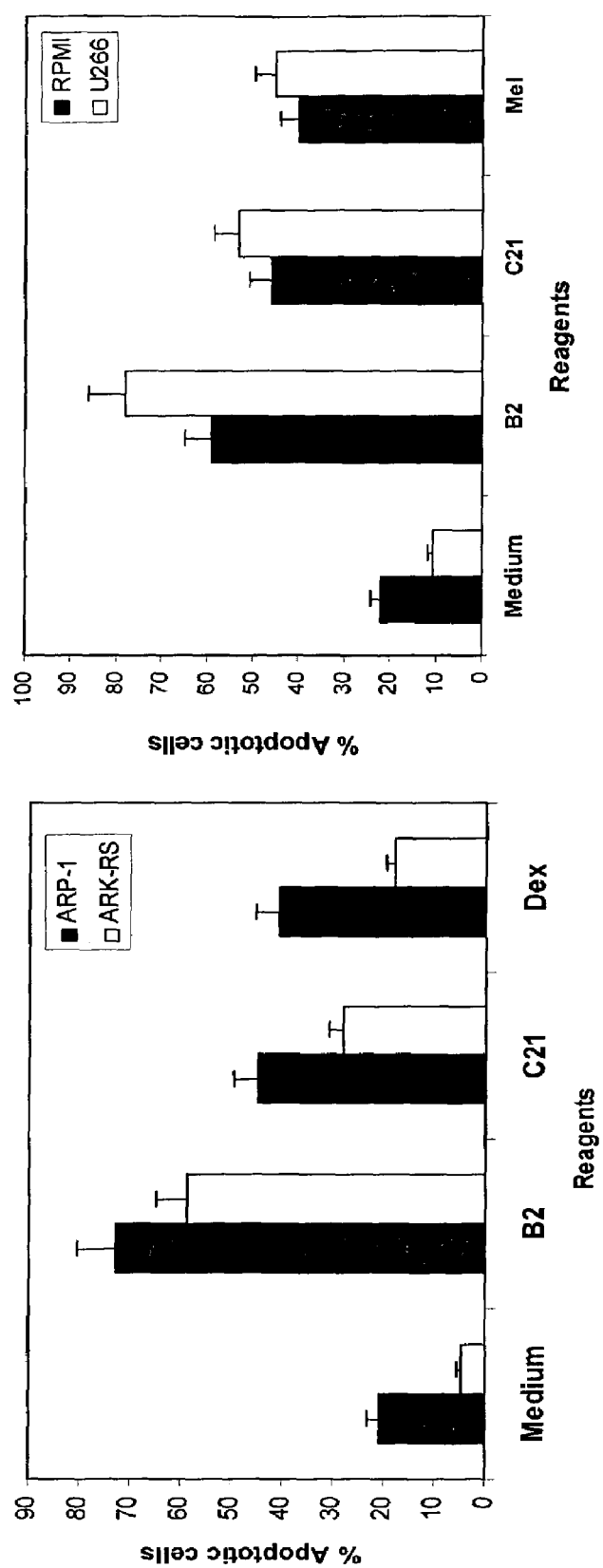
FIG. 15 compares the apoptotic effects of anti-$\beta_2$m antibodies (B2 and C21) to dexamethasone (Dex) and melphalan (Mel) in myeloma cells (ARP-1, ARK-RS, RPMI and U266) in accordance with an embodiment of the present invention.

Another problem common to many potential chemotherapeutic agents is a lack of efficacy. Melphalan and dexamethasone are chemotherapy agents commonly used for myeloma. For example, myeloma cell lines ARP-1 and ARK-RS are sensitive to dexamethasone, and RPMI-8226 and U266 are sensitive to melphalan. As shown in FIG. 15, the anti-$\beta_2$m antibodies have apoptotic effects that are at least as strong as, if not stronger than, the apoptotic effects of melphalan and dexamethasone. Additionally, both anti-$\beta_2$m antibodies are effective in each of the cell lines, and not just a subset.

$\beta_2$-Microglobulin Binding Agents Interact with Cell Surface HLA Class I Molecules on the Surface of Tumor Cells There may be multiple mechanisms by which $\beta_2$m binding agents suppress tumor growth. For example, in an embodiment, $\beta_2$-microglobulin binding agents prevent $\beta_2$m from interacting with HLA class I molecules on the surface of tumor cells.

Figure 16:
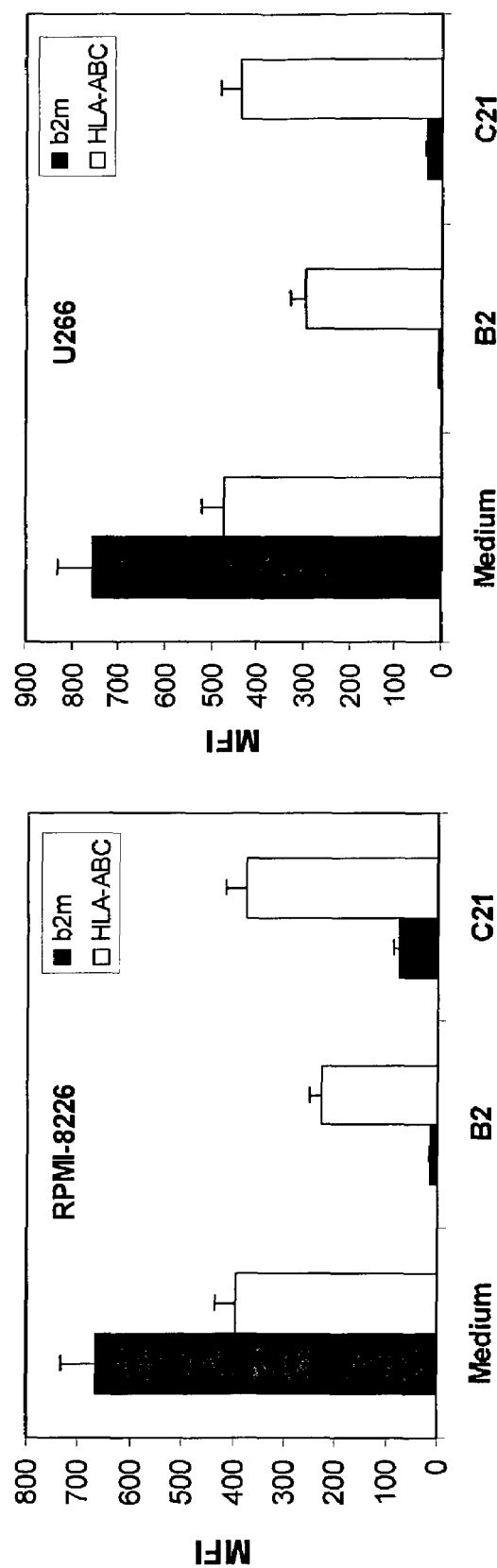
FIG. 16 illustrates that incubation with anti-$\beta_2$m antibodies B2 and C21 blocks the binding of FITC-conjugated anti-$\beta_2$m (■) and FITC-conjugated HLA-ABC (□) antibodies to the cell surface of myeloma cells (RPMI-8226 and U266) in accordance with an embodiment of the present invention, wherein MFI is the mean fluorescence intensity of FITC-antibody binding.

Thus, in an embodiment, anti-$\beta_2$m antibodies may bind to the cell surface via $\beta_2$m class I HLA molecules. For example, myeloma cells pre-incubated with B2 antibody show almost complete inhibition of the binding of fluorescein isothiocyanate (FITC)-labeled anti-$\beta_2$m antibody and partially reduced binding of FITC-labeled anti-HLA-ABC antibody (FIG. 16), suggesting that the B2 antibody blocks binding of other agents to MHC molecules on the cell surface. Also, cells incubated with C21 show significantly reduced binding of FITC-labeled anti-$\beta_2$m antibody (FIG. 16). Thus, in an embodiment, both B2 and C21 bind to $\beta_2$m on the surface of tumor cells. However, B2 binding almost completely blocks surface $\beta_2$m and partially blocks HLA-ABC, whereas C21 binding significantly blocks surface $\beta_2$m, but not HLA-ABC.

Figure 17:
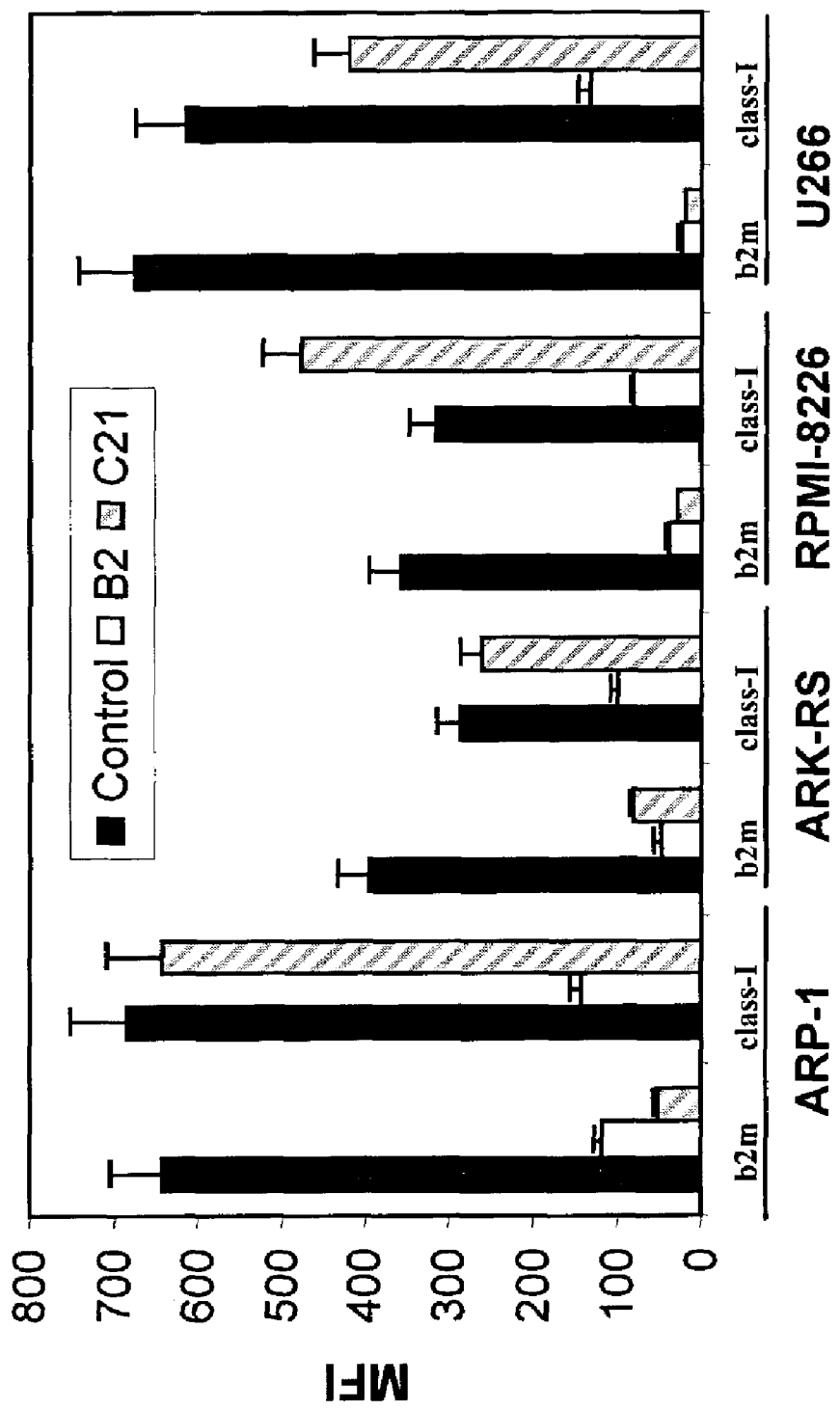
FIG. 17 illustrates changes in surface $\beta_2$m and HLA-ABC (class I) after treatment with anti-$\beta_2$m antibodies B2 or C21 in accordance with an embodiment of the present invention, wherein MFI is the mean fluorescence intensity of the anti-$\beta_2$m and anti-HLA-ABC (class-I) FITC-conjugated antibody (as indicated by groupings on the x-axis) which binds to cells treated with B2 or C21; control are cells exposed only to medium.

Alternatively or additionally, the anti-$\beta_2$m antibodies lead to a reduction of $\beta_2$m or class I molecules on the surface of the tumor cells, indicating that MHC class I molecules may be involved in $\beta_2$m- and anti-$\beta_2$m antibody—induced growth suppression and apoptosis in myeloma cells. In an embodiment, cells cultured in the presence of B2 and C21 anti-$\beta_2$m antibodies may have significantly lower levels of surface $\beta_2$m and/or HLA class I $\alpha$ chain on the cell surface than cells cultured in the absence of anti-$\beta_2$m antibodies (FIG. 17). For example, culturing of myeloma cells in the presence of B2 anti-$\beta_2$m antibody results in greater than 2-3 fold reduction in cell surface $\beta_2$m and $\alpha$ chain. In contrast, culturing of myeloma cells in the presence of C21 anti-$\beta_2$m antibody results reduction in cell surface $\beta_2$m, but less reduction in the cell surface $\alpha$ chain (FIG. 17).

Figure 18:
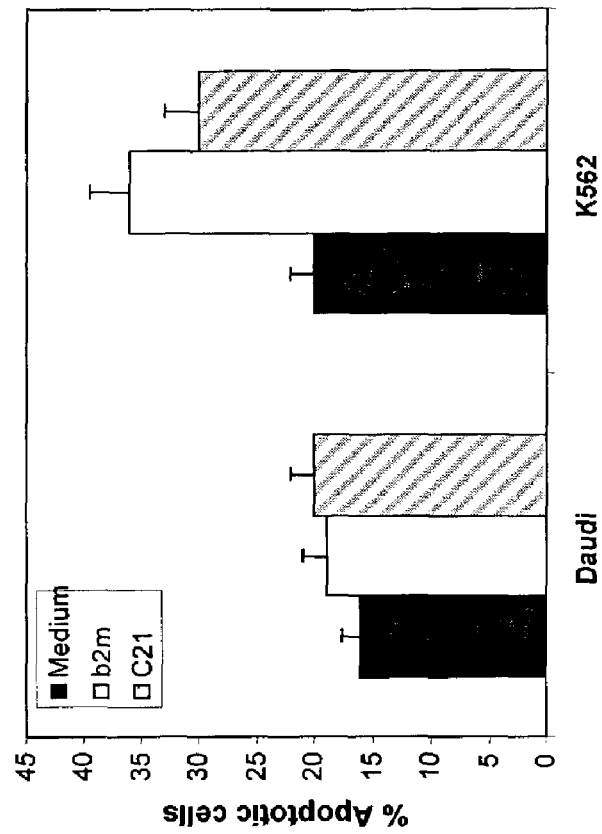
FIG. 18 illustrates that anti-$\beta_2$m antibodies also kill non-myeloma tumor cells, such as lymphoma and leukemia cells, that express surface MHC class I molecules in accordance with an embodiment of the present invention, wherein (A) shows HLA-ABC expression on Daudi cells and K562 leukemia cells, and (B) shows antibody-induced Annexin-V positive apoptotic cells.
Figure 18:
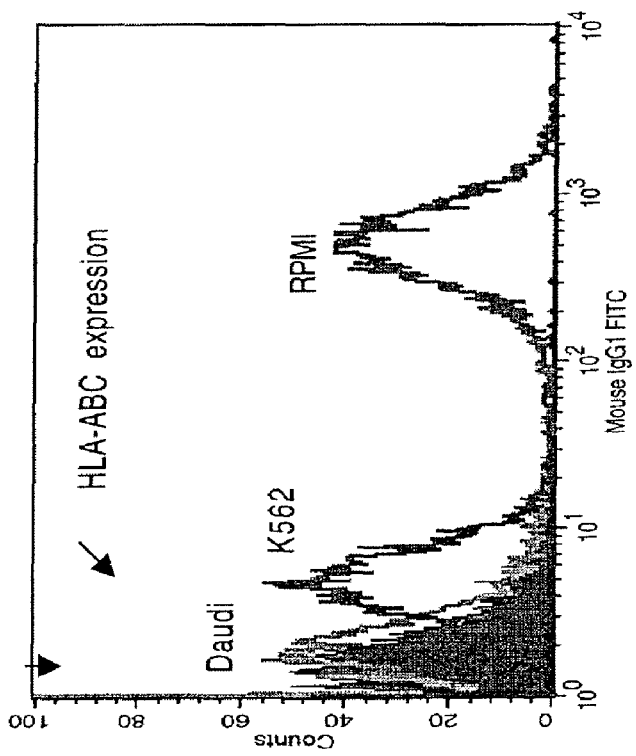

The present invention recognizes that the anti-proliferative effect of anti-$\beta_2$m antibodies is not limited to myeloma cells, but is found for other tumor cells having HLA class I molecules on the cell surface. For example, in an embodiment, anti-$\beta_2$m antibodies inhibit growth and proliferation of lymphoma, leukemia, and solid tumors including, but not limited to, breast cancer, melanoma, and colon cancer. As shown in FIG. 18, B2 and C21 anti-$\beta_2$m antibodies are not effective in inducing apoptosis in tumor cells that do not express HLA-ABC class I molecules (Daudi), but are effective in inducing apoptosis in K562 leukemia cells that express low levels of HLA-ABC class I molecules.

Therapeutics

The invention contemplates methods of administration of the compositions of the present invention which are well known in the art. A pharmaceutically acceptable carrier comprises substances commonly used in pharmaceutical formulations suitable for human use. For example, in an embodiment, administration of the compositions of the present invention is oral. Also, administration may employ a time-release capsule. In another embodiment, administration of the composition is by intravenous, intra-arterial, or intraperitoneal injection. In another embodiment, the method of administration is by a transdermal patch. In yet another embodiment, administration is as an aerosol. In another embodiment, administration is sublingual. In yet another embodiment, administration is transrectal, as by a suppository or the like.

Pharmaceutical formulations comprising pharmaceutically acceptable carriers can be prepared by procedures known in the art. For example, the compositions of the present invention can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivates; binding agents such as carboxymethyl cellulose and other cellulose derivatives, alginates, gelatin, and polyvinyl pyrrolidone; moisturizing agents such as glycerol; disintegrating agents such as agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compositions of the present invention can also be formulated as elixirs or solutions for convenient oral administration or as solutions appropriate for parenteral administration, for instance by intramuscular, subcutaneous or intravenous routes. For example, dissolution in a physiological solution such as a buffered saline is appropriate for intravenous administration. Additionally, the compounds are suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The therapeutic efficacy of exogenous compounds can be determined by standard pharmaceutical procedures in cell cultures or experimental animals using procedures known in the art. The dose ratio between toxic and therapeutic effects is the therapeutic index and may be expressed as $LD_{50}/ED_{50}$, wherein $LD_{50}$ is understood to represent the dose which is toxic to 50% of the subjects and $ED_{50}$ is understood to represent the dose which is effective in 50% of the subjects. Generally, compounds which exhibit large therapeutic indices are preferred. Administration of the compound may be hourly, daily, weekly, monthly, yearly or a single event.

In an embodiment, the dose of $\beta_2m$, $\beta_2m$-binding agent, or other MHC-binding agent required for inhibition of cancer cells comprises levels of the agent that may be used pharmacologically in animals and humans. For example, in preferred embodiments, the level of anti-$\beta_2m$ antibody at the tumor cells comprises from 0.1 µg/ml to 2,000 µg/ml, more preferably, from 1 µg/ml to 500 µg/ml, and even more preferably, from 5 µg/ml to 200 µg/ml. Alternatively, in preferred embodiments, the level of $\beta_2m$ at the tumor cells comprises from 0.1 µg/ml to 2,000 µg/ml, more preferably, from 1 µg/ml to 200 µg/ml, and even more preferably, from 5 µg/ml to 100 µg/ml.

Also, the ability of $\beta_2m$, a $\beta_2m$-binding agent, or other MHC-binding agents to inhibit tumor growth may a function of cell division and the length of the cell cycle. Thus, application of the $\beta_2m$, $\beta_2m$-binding agent, or other MHC-binding agent may be hourly, daily, or over the course of weeks. Thus, preferably, the effective amount of the $\beta_2m$, $\beta_2m$-binding agent, or other MHC-binding agent comprises from about 1 ng/kg body weight to about 300 mg/kg body weight. More preferably, the effective amount of the $\beta_2m$, $\beta_2m$-binding agent, or other MHC-binding agent comprises from about 1 µg/kg body weight to about 100 mg/kg body weight. Even more preferably, the effective amount of the $\beta_2m$, a $\beta_2m$-binding agent, or other MHC-binding agent comprises from about 10 µg/kg body weight to about 50 mg/kg body weight.

Alternatively, a continuous level of $\beta_2m$, a $\beta_2m$-binding agent, or other MHC-binding ranging from about 0.005-10,000 µg/kg/hour, or more preferably, 0.1-2,000 µg/kg/hr, or even more preferably 1.0-1,000 µg/kg/hour may be employed. The actual effective amount will be established by dose/response assays using methods standard in the art. Thus, as is known to those in the art, the effective amount will depend on bioavailability, bioactivity, and biodegradability of the compound.

EXAMPLES

The present invention may be better understood by reference to the following non-limiting examples.

Example 1

Materials and Methods

A. Reagents

Purified human $\beta_2m$ was purchased from Sigma Corp. (St. Louis, Mo.). According to information from the manufacturer, the protein is purified from human urine, and its purity is >98% by sodium dodecyl sulfate-polyacrylamide gel electrophoresis (SDS-PAGE). To ensure its purity, the $\beta_2m$ protein (10 µg) was analyzed by SDS-PAGE with a 4.5% stacking and 15% resolving gel under denaturing conditions; no contaminating proteins were detected (data not shown).

Neutralizing monoclonal antibodies against Fas (clone ZB4), tumor necrosis factor (TNF) receptor (TNFR, clone 16803.1), and TNF-related apoptosis-inducing ligand (TRAIL) receptor-2 (TRAILR-2) were purchased from Immunotech (Marseille, France), Oncogene Research Products (Boston, Mass.), and Calbiochem-Novabiochem Corp. (La Jolla, Calif.), respectively. Antibodies against $\beta_2m$ (clones B2 and C21) were obtained from Serotec Ltd. (Oxford, UK), and an MHC-blocking antibody, W6/32, was kindly provided by Dr. M. Cannon (Department of Immunology and Microbiology, University of Arkansas for Medical Sciences, Little Rock, Ark.). Antibodies that contain sodium azide were dialyzed against phosphate-buffered saline (PBS) overnight.

B. Myeloma Cell Lines and Primary Tumor Cells

The U266, RPMI-8226, ARH-77, and IM-9 human myeloma-derived cell lines were obtained from the American Type Culture Collection (Rockville, Md.). The ARP-1 and ARK-RS cell lines were established at the Arkansas Cancer Research Center from bone marrow aspirates of patients with MM (Harding, J., et al., *Blood*, 84:3063-3070, 1994) and provided by Dr. J. Epstein. These cell lines, except ARH-77 and IM-9, are negative for Epstein-Barr virus (EBV). Cells were cultured in RPMI-1640 (Gibco, Grand Island, NY) containing 10% heat-inactivated (56° C. for 30 min) fetal bovine serum, 100 U/ml penicillin, 100 µg/ml streptomycin, and 4 mmol L-glutamine (Gibco).

Primary myeloma cells were isolated from bone marrow aspirates obtained from patients during a routine clinic visit. Institutional Research Board-approved consent forms are kept on file. Briefly, bone marrow mononuclear cells were separated by Ficoll-Paque (Amersham Pharmacia Biotech, Piscataway, N.J.) density-gradient centrifugation. CD138+ cells were isolated by incubation with anti-CD138 antibody-conjugated microbeads and sorted by VarioMACS magnetic cell-sorting kit (Miltenyi Biotec GmbH, Bergisch Gladbach, Germany), according to the manufacturer's recommendations. The sorted CD138+ cell populations contained >90% myeloma plasma cells (Yi, Q., et al., *Blood*, 90:1960-1967, 1997). Freshly sorted cells were used in most of the experiments.

C. Cell Proliferation or Growth Assay

Myeloma cells ($1 \times 10^5$/ml for cell lines and $0.5-1 \times 10^6$/ml for primary cells) were cultured in complete medium. For experiments with $\beta_2$m or anti-$\beta_2$m antibody that bind $\beta_2$m, cells were cultured in the absence or the presence of $\beta_2$m for up to 120 hours or anti-$\beta_2$m antibody for up to 48 hours. Viable cells were determined by trypan blue (Gibco) exclusion. DNA synthesis was assayed by $^3$H-thymidine incorporation using 1 μCi/well of $^3$H-thymidine (Dupont-NEN; NEN Life Science Products, Inc., Boston, Mass.) added 6 hours before harvesting onto glass fiber filters. Radioactivity was measured in a liquid scintillation analyzer (Packard, Meriden, Conn.). Experiments were performed in triplicate, and cell growth was expressed as a percentage of that seen in control media.

D. Apoptosis Assays and Caspase Inhibitor

The fraction of apoptotic cells was determined by staining cells with Annexin V-fluorescein isothiocyanate (FITC) (Immunotech) and propidium iodide (PI) (Sigma) (Vermes, I., et al., *J. Immunol. Methods*, 184:39-51, 1995). Myeloma cells were incubated in medium containing various concentrations of $\beta_2$m, or anti-$\beta_2$m antibody, or both, for 48 hours and then resuspended in Annexin V-binding buffer. 5 μl of Annexin V-FITC (BD PharMingen, San Diego, Calif.) were added and incubated for 30 minutes. After washing and re-suspension of the cells in the binding buffer, 5 μl of PI were added, and the cells were ready for analysis. Percentages of apoptotic cells are the sum of PI$^-$/Annexin V$^+$ (newly apoptotic) and PI$^+$/Annexin V$^+$ (already apoptotic) cell populations (Vermes, I., et al., *J. Immunol. Methods*, 184:39-51, 1995).

To confirm cell apoptosis induced by $\beta_2$m and anti-$\beta_2$m antibodies, the terminal deoxynucleotidyl transferase-mediated dUTP nick end labeling (TUNEL) assay was also employed. A flow cytometry-based cell death detection kit (APO-BRDU) was purchased from BD PharMingen, and experiments were performed according to the manufacturer's protocol.

E. Caspase Inhibitor

A pan-caspase inhibitor, z-Val-Ala-Asp-fluoromethyl ketone (Z-VAD-FMK) or caspase I inhibitor V, was purchased from Calbiochem-Novabiochem. This peptide was dissolved in dimethylsulfoxide (DMSO, Sigma) and added to cell suspensions at a final concentration of 100 μM (final DMSO concentration of 0.25%).

F. Cell Cycle Analysis

To determine the effect of $\beta_2$m, or anti-$\beta_2$m antibodies, on cell cycle progression, 5-bromo-2'-deoxyuridine (BrdU, Sigma) incorporation was used (Gratzner, H. G., *Science*, 218:474-475, 1982). Briefly, after treatment with the agent of interest, cells were incubated for 2 hours with 20 μM BrdU, fixed with 70% ethanol overnight, washed with PBS, and incubated in 2 M hydrochloride for 20 minutes. After washing, FITC-conjugated anti-BrdU antibody (Becton Dickinson, Franklin Lakes, N.J.) was added and incubated for 20 minutes, followed by washing and incubation with ribonuclease (100 μg/ml RNase, Sigma) and PI (50 μg/ml). Cells were analyzed by flow cytometry.

G. Flow Cytometry Analysis of Cell Surface Antigens

The expression of various surface molecules, such as HLA-ABC, $\beta_2$m, Fas, and FasL, was determined by direct immunofluorescence using antibodies conjugated with FITC (anti-HLA-ABC and anti-Fas, Immunotech; anti-$\beta_2$m, Sigma) and phycoerythrin (PE) (anti-FasL, Caltag Laboratories, Burlingame, Calif.). After staining, cells were resuspended in PBS and analyzed by a FACScan flow cytometer (Becton Dickinson), as described previously (Yi, Q., et al., *Neurology*, 42:1081-1084, 1992).

H. Western Blotting Detection of Cyclins

Cells were cultured with or without 40 μg/ml $\beta_2$m for 48 hours, harvested, washed, and lysed with lysis buffer (50 mM Tris, pH 7.5, 140 mM NaCl, 5 mM EDTA, 5 mM NaN$_3$, 1% Triton-X-100, 1% NP-40, 1× protease inhibitor cocktail). To detect cyclins A, D (D1 and D2), and E, cell lysates were subjected to SDS-PAGE, transferred to polyvinylidene difluoride membrane, and immunoblotted with respective anticyclin antibodies (Santa Cruz Biotechnology, Inc., Santa Cruz, Calif.). The membrane was stripped and reprobed with anti-β-actin antibody (Santa Cruz Biotechnology) to ensure equivalent protein loading. For detection of caspase-3 activation and cleavage of poly(ADP-ribose) polymerase (PARP), the membranes were immunoblotted with anti-caspase-3 antibody (Santa Cruz Biotechnology) or anti-PARP antibody (BD PharMingen). Secondary antibodies conjugated to horseradish peroxidase were used for detection, followed by enhanced chemiluminescence (Bio-Rad Laboratories, Hercules, Calif.) and autoradiography.

I. Statistical Analysis

The Student's t test was used to compare various experimental groups; significance was set at $P<0.05$.

Example 2

$\beta_2$m Suppresses the Growth of Myeloma Cells in Vitro

These experiments investigated whether $\beta_2$m suppresses the growth of myeloma cells. Pure myeloma cells are completely free of Epstein Barr Virus (EBV$^-$), whereas other tumor cell types may be EBV$^+$. Initial experiments tested the effect of $\beta_2$m on the growth of four EBV-negative myeloma cell lines. The proliferation of ARK-RS, ARP-1, RPMI-8226, and U266 cells was suppressed by $\beta_2$m in a dose-dependent (FIG. 1A) and time-dependent (FIG. 1B) manner, as detected by $^3$H-thymidine incorporation assay ($P<0.05$ and 0.01, respectively) and viable cell counts (data not shown). $\beta_2$m also suppressed the growth of two EBV-positive cell lines derived from myeloma patients, ARH-77 and IM-9 ($P<0.05$ and 0.01, respectively) (FIG. 1C). These results indicate that $\beta_2$m can also affect non-myeloma cells such as lymphoma cells. To ensure that the growth-regulatory effect was indeed mediated by $\beta_2$m, other highly purified human urine $\beta_2$m from Calbiochem-Novabiochem and a recombinant human $\beta_2$m from Serotec on these cells were tested and similar results were obtained (data not shown).

Next, the effect of $\beta_2$m on primary myeloma cells was examined. Purified tumor cells from 5 patients with MM were cultured for 24 hours in the presence of various concentrations of $\beta_2$m. As shown in FIG. 2, $\beta_2$m inhibited the proliferation of cells from 4 of these patients in a dose-dependent manner (patient nos. 1, 2, 4, and 5; P<0.05). $\beta_2$m had no apparent effect on cells from patient no. 3. Primary myeloma cells from 3 patients (nos. 1, 3, and 5) were tested twice, and similar results were obtained (data not shown), indicating a high reproducibility of the results. Thus, $\beta_2$m was found to suppress ex vivo the growth of primary myeloma cells from a majority of MM patients.

Example 3

$\beta_2$m Induces Apoptosis in Myeloma Cells

In addition to growth inhibition, $\beta_2$m also induces apoptosis in myeloma cells. As exemplified by the experiments depicted in FIG. 3, the addition of $\beta_2$m led to a significant induction of apoptosis (P<0.01) in myeloma cells (RPMI-8226), as determined by Annexin V and PI staining (FIG. 3A) and TUNEL assay (FIG. 3B). The induction of apoptosis was dose-dependent (FIG. 3C). A summary of $\beta_2$m-induced apoptosis in all six cell lines is shown in FIG. 3D. The degree of apoptosis was higher in RPMI-8226, ARK-RS, and ARH-77 cells (P<0.01, p<0.05, and p<0.05, respectively) than in other cell lines. These results were confirmed by both apoptosis assays.

Induction of apoptosis in primary myeloma cells by $\beta_2$m was examined in two patients (nos. 1 and 5), as enough cells were obtained from these two patients. The addition of 20 µg/ml $\beta_2$m to these primary myeloma cells for 24 hours resulted in an increase in apoptotic cells. Thus, 20% of the untreated cells from patient 1 were apoptotic as opposed to 38% of the treated cells. Also, 30% of the untreated cells from patient 5 were apoptotic, versus 45% of the treated cells. These results are consistent with the cell proliferation data discussed above.

Interleukin-6 (IL-6) and insulin-like growth factor I (IGF-I) are growth and survival factors for myeloma cells (Kawano et al., *Nature*, 332:83-85, 1988; Harding et al., *Blood*, 84:3063-3070, 1994; Georgii-Hemming et al., *Blood*, 88:2250-2258, 1996). Tests were conducted to determine whether the addition of recombinant human IL-6 or IGF-I (both from R&D Systems, Inc., Minneapolis, Minn.) to cultures may counteract the effects of $\beta_2$m on myeloma cells. Representative results are shown in FIG. 4, and demonstrate that while addition of IL-6 (20 ng/ml) or IGF-I (50 ng/ml) reduced the percentage of cells undergoing spontaneous apoptosis, only IL-6 protected myeloma cells from $\beta_2$m-induced apoptosis.

Example 4

$\beta_2$m-Induced Apoptosis Depends on Caspase Activation

Various types of apoptosis, such as receptor-mediated or stress-induced apoptosis, depend on the activation of caspases. To investigate whether caspase cascades participate in $\beta_2$m-induced apoptosis, activation of caspase-3 and subsequent cleavage of PARP were investigated by Western blotting with specific antibodies. Treatment of cells with $\beta_2$m resulted in activation and processing of caspase-3 and cleavage of PARP in ARK-RS, ARP-1, and RPMI-8226 cells, but not in U266 cells (FIG. 5A). When the pan-caspase inhibitor Z-VAD-FMK was added to the culture, activation and processing of caspase-3 (data not shown), cleavage of PARP (FIG. 5B), and apoptosis (FIG. 5C) were inhibited. As a control, this caspase inhibitor also abrogated apoptosis induced by the anti-Fas antibody 7C11 (IgM, Immunotech) in Jurkat cells (FIG. 5D). Thus, these results demonstrate that $\beta_2$m-induced apoptosis in myeloma cells involves caspase cascades.

Example 5

$\beta_2$m-Induced Apoptosis is Independent of Fas/FasL, TNF-α/TNFR, and TRAIL/TRAILR-2 Systems To investigate whether $\beta_2$m-induced apoptosis is mediated by the Fas/FasL, TNF-α/TNFR, or TRAIL/TRAILR-2 systems, the effect of neutralizing antibodies against Fas, TNFR, or TRAILR-2 was examined, with each at a concentration of 10 µg/ml. In the preliminary studies, the antibodies were able to block FasL- and TRAIL-induced apoptosis in Jurkat and ARP-1 myeloma cells (data not shown). Because $\beta_2$m had strong effects on ARK-RS and RPMI-8226 cells, these two cell lines were chosen for the studies. None of the neutralizing antibodies had an inhibitory effect on $\beta_2$m-induced apoptosis in the tumor cells (data not shown), suggesting that these pathways are not involved. These results are supported by flow cytometry analysis showing that only 1-5% of the myeloma cells expressed Fas or FasL. After treatment with $\beta_2$m, no obvious upregulation of the antigens was noted (data not shown). Furthermore, the anti-Fas antibody 7C11, which has a strong apoptosis-inducing effect on Jurkat cells (FIG. 5D), had no effect on the myeloma cells (data not shown).

Example 6

$\beta_2$m Arrests Cell Cycle Progression

Cell cycle analysis of exponentially growing cells demonstrates that treatment with $\beta_2$m for 48 hours results in alterations in cell cycle distribution. An increased percentage of cells in $G_0/G_1$ phases and a decreased percentage in S and $G_2$/M phases were observed in ARK-RS, ARP-1, and RPMI-8226 cells, but not in U266 cells (FIG. 6A), suggesting that a $G_0/G_1$ growth arrest was induced in these three cell lines. Furthermore, Western blot analysis revealed that $\beta_2$m treatment downregulated cyclins A and D2, but not cyclins D1 or E, in these three cell lines (FIG. 6B), providing further support for $\beta_2$m-induced growth arrest in myeloma cells. Taken together, these findings indicate that $\beta_2$m affects the growth and survival of most myeloma cell lines and primary tumor cells by inhibiting cell proliferation and inducing apoptosis and growth arrest in the tumor cells.

Example 7

Anti-$\beta_2$m Antibodies Suppress Tumor Cell Growth and Induce Apoptosis in Myeloma Cells To examine whether anti-$\beta_2$m antibodies had any effect on myeloma cell growth or proliferation, or could block the effect of $\beta_2$m, two commercially available B2 and C21 monoclonal antibodies (both from Serotec Inc., Raleigh, N.C.) were used. Antibody B2 binds to both soluble and surface-bound $\beta_2$m, and antibody C21 appears to bind only to soluble $\beta_2$m (Liabeuf, A., et al., *J. Immunol.*, 127:1542-1548, 1981). W6/32, an antibody that binds to mature class I molecules (Ladasky, J. J., et al., *Immunogenetics*, 49:312-320, 1999), and purified mouse IgG, were used as controls.

Surprisingly, addition of anti-$\beta_2$m antibodies to myeloma cell cultures strongly suppressed the growth of established myeloma cell lines (FIG. 7A) and primary myeloma cells from patients (FIG. 7B). The effect was stronger with B2 antibody than C21, but both antibodies significantly inhibited cell growth. Data were obtained with antibodies at 100 μg/ml in 48-hour culture, and the $^3$H-thymidine incorporation assay was used.

As shown by the experiments depicted in FIG. 8A, both antibodies B2 and C21 induced apoptosis (P<0.01) on RPMI-8226 cells (P<0.01). Also, surprisingly, it was found that the apoptotic effects of $\beta_2$m was not prevented by anti-$\beta_2$m antibodies. In fact, the apoptotic effect of $\beta_2$m was enhanced by C21 ant-$\beta_2$m antibody (FIG. 8B). These results suggest that there is complex mode of interaction at the tumor cell surface for various components of the MHC $\beta_2$m HLA class I molecules, which when disrupted, can lead to cell death.

Significant induction of apoptosis by the antibodies was also observed at about a 10-fold lower concentration (12.5 μg/ml) of the antibodies and in other cell lines, including ARK-RS and RPMI-8226 (FIG. 9). Incubation of the cells with W6/32 or mouse IgG did not induce apoptosis in myeloma cells (FIG. 8).

The apoptotic response was dose-dependent (FIG. 9) and time-dependent (data not shown). Four established myeloma cell lines (ARP-1, ARK-RS, RPM1, U266) and primary myeloma cells from five patients (Pats. 1-5) were found to be sensitive to anti-$\beta_2$m antibody-induced apoptosis (FIG. 10). In these experiments, data were obtained with antibodies at 100 μg/ml in a 48-hour culture for myeloma cell lines or in a 24-hour culture for primary myeloma cells. The apoptotic effect of the antibodies was not counteracted by IL-6 or IGF-I (FIG. 11). This insensitivity to cytokines was observed even when the cells were preincubated with the cytokines for 4 hours before the anti-$\beta_2$m antibodies were added (data not shown). The apoptosis-inducing effect was not restricted to these two anti-$\beta_2$m antibodies, as similar results were obtained with other commercially available anti-$\beta_2$m antibodies (data not shown).

Example 8

$\beta_2$m Does Not Block the Apoptotic Effects of Anti-$\beta_2$m Antibodies

As both $\beta_2$m and anti-$\beta_2$m antibodies induced apoptosis in myeloma cells, experiments were performed to examine whether preincubating $\beta_2$m and anti-$\beta_2$m antibodies could reduce the apoptotic capacity of anti-$\beta_2$m antibodies. FIG. 12 depicts a representative experiment in which the anti-$\beta_2$m antibodies (50 μg/ml; molecular weight of IgG: 150 kDa) were preincubated with much higher molar concentrations of $\beta_2$m (12.5-50 μg/ml; molecular weight of $\beta_2$m: 11.6 kDa) before cells were added. The apoptosis-inducing effect of antibody B2 was slightly reduced by $\beta_2$m, while that of antibody C21 was enhanced by addition of $\beta_2$m. These results were reproduced in numerous experiments using the same or different myeloma cells. These findings indicate that the presence of high concentrations of soluble $\beta_2$m in myeloma patients will not compromise the therapeutic potential of anti-$\beta_2$m antibodies.

Example 9

Anti-$\beta_2$m Antibodies Do Not Kill Normal Hematopoietic Cells

Figure 13:
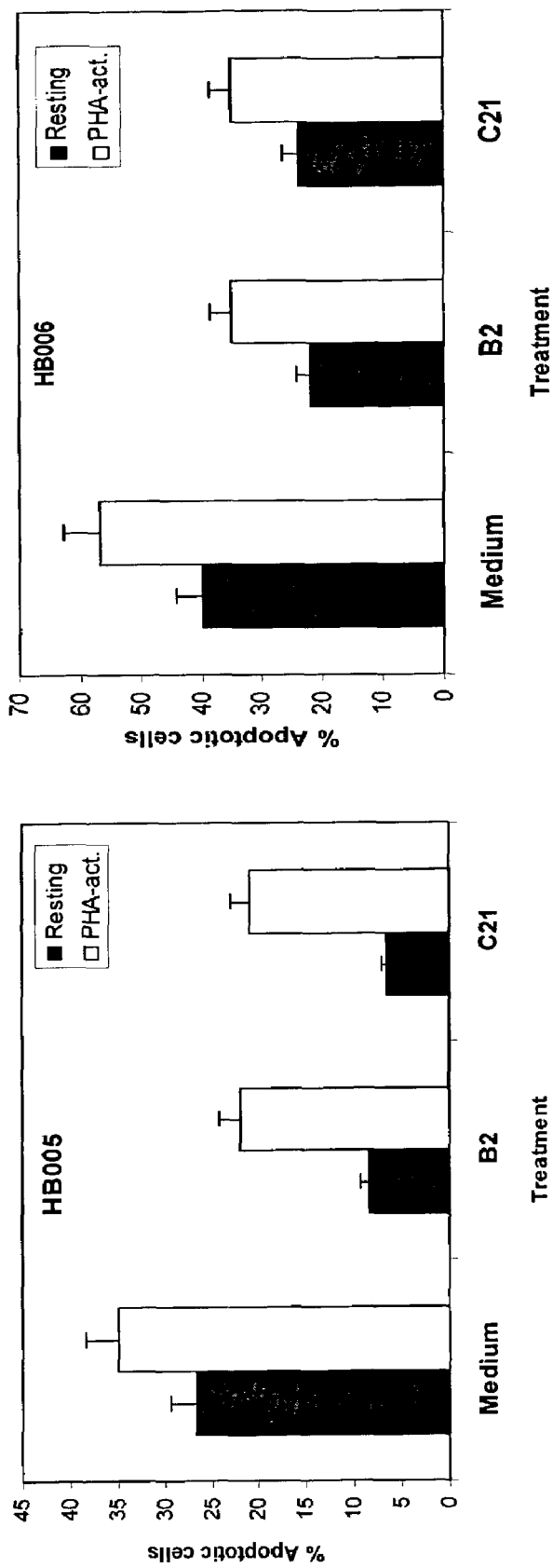
FIG. 13 illustrates that anti-$\beta_2$m antibodies (B2 and C21) do not kill normal blood lymphocytes in accordance with an embodiment of the present invention, wherein blood lymphocytes from healthy individuals, either resting (■) or phytohemagglutinin-activated (□) (PHA-act.; 3 µg/ml for 3 days), were incubated with 100 µg/ml of either B2 or C21 antibody for 48 hours.
Figure 14:
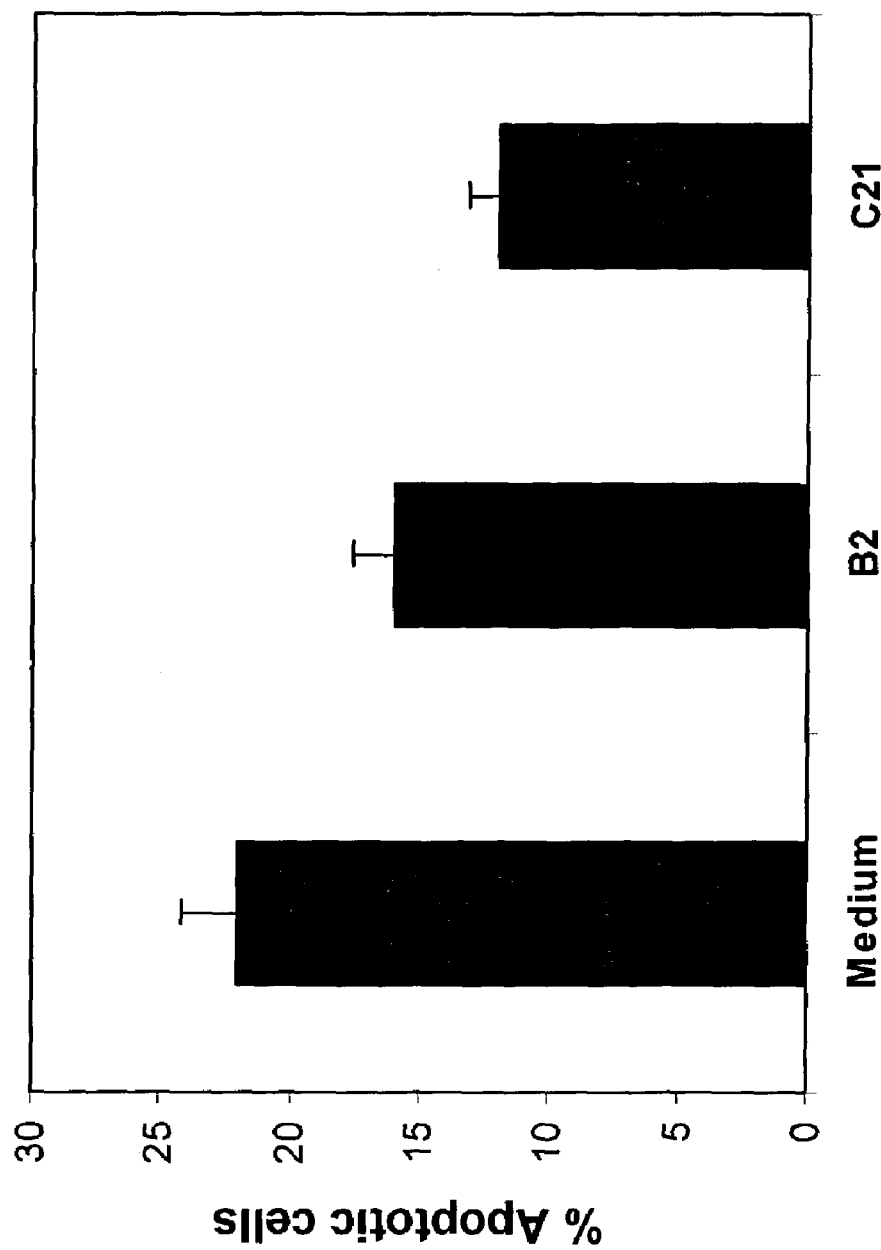
FIG. 14 illustrates that anti-$\beta_2$m antibodies B2 and C21 do not increase apoptosis in normal CD34$^+$ stem cells in accordance with an embodiment of the present invention.

To determine whether anti-$\beta_2$m-antibodies can be used clinically, experiments were performed to examine whether the antibodies would be toxic (i.e., induce apoptosis) in normal blood cells. Incubation of blood lymphocytes from healthy individuals, using either resting or phytohemagglutinin (3 μg/ml for 3 days)-activated cells (PHA-act.), with 100 μg/ml of either B2 or C21 antibody for 48 hours did not increase the percentage of apoptotic cells (FIG. 13, data from two healthy donors). Rather, the treatment decreased the percentage of apoptotic cells compared with that of culture with medium only. More importantly, purified bone marrow CD34$^+$ stem cells from healthy individuals (purchased from BioWhittaker Inc., Walkersville, Md.) were also resistant to anti-$\beta_2$m antibody-mediated apoptosis (FIG. 14). Interestingly, as with lymphocytes, addition of the antibodies (100 μg/ml) also reduced the percentages of apoptotic stem cells. These results suggest that anti-$\beta_2$m antibodies do not kill normal hematopoietic cells, including CD34$^+$ stem cells.

Example 10

Anti-$\beta_2$m Antibody-induced Apoptosis in Myeloma Cells is Stronger than that Observed with Melphalan and Dexamethasone Melphalan and dexamethasone are commonly used chemotherapy drugs for myeloma. Myeloma cell lines ARP-1 and ARK-RS are sensitive to dexamethasone, and RPMI-8226 and U266 are sensitive to melphalan. To investigate the potential potency of anti-$\beta_2$m antibodies in relation to known chemotherapeutics, killing of myeloma cells by anti-$\beta_2$m antibodies was compared to killing of these cells by the chemotherapy agents. As shown in FIG. 15, the anti-$\beta_2$m antibodies (100 μg/ml), especially B2, had apoptosis-inducing effects that were at least as strong as the chemotherapy drugs, even though the drug concentrations were higher (20-100 μM) than typically employed in vitro (1-10 μM) (Georgii-Hemming, P., et al., *Blood,* 88:2250-2258, 1996; Harding, J., et al., *Blood,* 84:3063-3070, 1994). Additionally, both antibodies displayed apoptotic effects on all four of the cell lines. These results suggest that anti-$\beta_2$m antibodies may be more potent than these two chemotherapy drugs in killing myeloma cells.

Example 11

Modulation of Surface Class I Molecules on Myeloma Cells by Anti$\beta_2$m Antibodies—Both B2 and C21 Bind to Surface $\beta_2$M Experiments were performed to test whether anti-$\beta_2$m antibodies can bind to the cell surface and block the subsequent binding of the FITC-conjugated antibodies to cell surface recognition sites. Myeloma cells were incubated with B2 or C21 antibodies at 4° C. (on ice) for 30 minutes, washed three times, and stained with the FITC-conjugated antibodies. As shown in FIG. 16, cells incubated with B2 show almost complete inhibition of the binding of FITC-conjugated anti-$\beta_2$m antibody and partially reduced binding of FITC-conjugated anti-HLA-ABC antibody. Cells incubated with C21 also had significantly reduced binding of FITC-conjugated anti-$\beta_2$m antibody, but the binding of FITC-conjugated anti-HLA-ABC antibody was not affected. These results suggest that both B2 and C21 bind to surface $\beta_2$m. However, B2 binding almost completely blocks surface $\beta_2$m and partially blocks HLA-ABC, whereas C21 binding significantly blocks surface $\beta_2$m but not HLA-ABC.

Experiments were also performed to investigate whether anti-$\beta_2$m antibodies can alter Class I MHC molecules on the cell surface. Myeloma cells were cultured with or without anti-$\beta_2$m antibodies (100 µg/ml) for 48 hours and analyzed for the surface expression of MHC class I molecules with the use of fluorescein isothiocyanate (FITC)-conjugated anti-$\beta_2$m antibody (GJ14; Oxford Biotechnology Ltd., Raleigh, N.C.) and anti-HLA-ABC antibody (clone B9.12.1, recognizing a monomorphic epitope common to HLA-A, -B and -C molecules; Immunotech Inc., Miami, Fla.). As shown in FIG. 17, it was found that treatment of the cells with antibody B2 resulted in a significant reduction in the binding of FITC-conjugated anti-$\beta_2$m and FITC-conjugated anti-HLA-ABC antibodies to the cell surface. In contrast, treatment with antibody C21 significantly reduced the binding of FITC-conjugated anti-$\beta_2$m antibodies, but not the binding of FITC-conjugated anti-HLA-ABC antibodies. Treatment with control antibody W6/32 had no effect on the level of surface $\beta_2$m or the $\alpha$ chain (data not shown). Previous work suggests that C21 anti-$\beta_2$m antibody cannot bind to the cell surface (Liabeuf, A., et al., *J. Immunol.*, 127:1542-1548, 1981). Thus, the data suggests that anti-$\beta_2$m antibody B2 binds to surface $\beta_2$m and blocks the binding of staining antibodies and/or downregulates surface HLA-ABC molecules, whereas C21 depletes surface $\beta_2$m from class I molecules.

The determination that the binding of B2 and C21 significantly blocks surface $\beta_2$m (FIG. 16) may explain the observed dramatic reduction of surface $\beta_2$m (FIG. 17). A reduction in surface HLA-ABC molecules, however, was also noted on the cell surface after B2 treatment (FIG. 17), which might be a result of partial blockage of the HLA-ABC molecules by B2 binding to $\beta_2$m (FIG. 16) and/or a decreased density of the molecules.

Example 12

Effects of B2 and C21 on Daudi and K562 Cells

Because MHC class I molecules are implicated in the mechanism of $\beta_2$-mediated apoptosis, experiments were performed to determine whether anti-$\beta_2$m antibodies would prevent the growth of tumor cells that express low levels of class I molecules or do not express any class I molecules. HLA-ABC is absent on Daudi cells, due to a defect in $\beta_2$m mRNA expression, and is only weakly expressed on K562 leukemia cells (FIG. 18A). In these experiments, Daudi and K562 cells were incubated with B2 and C21 (100 µg/ml) and analyzed for the percentage of apoptotic cells measured as Annexin-V-positive cells after culture. As shown in FIG. 18B, anti-$\beta_2$m antibodies had no obvious effect on Daudi cells, but were able to kill a small percentage of the K562 leukemia cells. As K562 cells express a low level of HLA-ABC and perhaps other MHC class I molecules, they are more sensitive to B2-induced apoptosis. The results are consistent with the evidence indicating that B2 may be more potent than C21 in killing HLA-ABC-positive myeloma cells, and that anti-$\beta_2$m antibodies mediate their effects, at least in part, via MHC class I molecules. These results also indicate that anti-$\beta_2$m antibodies are effective against non-myeloma cells that express HLA-ABC molecules.

It should be understood that various changes and modifications to the presently preferred embodiments described herein will be apparent to those skilled in the art. Such changes and modifications can be made without departing from the spirit and scope of the present invention and without diminishing its attendant advantages.

What is claimed is:

1. A method to reduce growth or proliferation of one or more of multiple myeloma, lymphoma, or leukemia tumor cells in an individual in need thereof comprising administering to the individual a pharmacologically effective amount of an antibody in a pharmaceutically acceptable carrier, wherein the antibody binds to $\beta_2$-microglobulin and interacts with MHC $\beta_2$-microglobulin HLA class I molecules located on the multiple myeloma, lymphoma, and/or leukemia tumor cells, and wherein a pharmacologically effective amount of the antibody comprises sufficient antibody to reduce proliferation of the multiple myeloma, lymphoma, and/or leukemia tumor cells.

2. The method of claim 1, wherein the antibody comprises a monoclonal antibody that binds $\beta_2$-microglobulin.

3. The method of claim 1, wherein the pharmacologically effective amount of the antibody reduces proliferation of the multiple myeloma, lymphoma, and/or leukemia tumor cells by over 50%.

4. The method of claim 1, wherein the pharmacologically effective amount of the antibody reduces proliferation of the multiple myeloma, lymphoma, and/or leukemia tumor cells by over 75%.

5. The method of claim 1, wherein the pharmacologically effective amount of the antibody reduces proliferation of the multiple myeloma, lymphoma, and/or leukemia tumor cells by over 90%.

6. The method of claim 1, wherein the pharmacologically effective amount of the antibody binds to MHC $\beta_2$-microglobulin HLA class I molecules located on the multiple myeloma, lymphoma, and/or leukemia tumor cells.

7. The method of claim 1, wherein the pharmacologically effective amount of the antibody reduces the number of MHC $\beta_2$-microglobulin HLA class I molecules located on the multiple myeloma, lymphoma, and/or leukemia tumor cells.

8. The method of claim 1, wherein the pharmacologically effective amount of the antibody stimulates apoptosis in the multiple myeloma, lymphoma, and/or leukemia tumor cells.

9. The method of claim 8, wherein the apoptosis promoting effects of the antibody are mediated at least in part by activation of caspases.

10. The method of claim 1, wherein the pharmacologically effective amount of the antibody causes changes in the cell cycle distribution of the multiple myeloma, lymphoma, and/or leukemia tumor cells.

11. A method to reduce growth or proliferation of one or more of multiple myeloma, lymphoma, or leukemia tumor cells in an individual in need thereof comprising administering to the individual a pharmacologically effective amount of an antibody in a pharmaceutically acceptable carrier, wherein the antibody binds to $\beta_2$-microglobulin, and wherein a pharmacologically effective amount of the antibody to $\beta_2$-microglobulin comprises sufficient antibody to reduce proliferation of the multiple myeloma, lymphoma, and/or leukemia tumor cells.

12. The method of claim 11, wherein the antibody that binds to $\beta_2$-microglobulin comprises a monoclonal antibody to $\beta_2$-microglobulin.

13. The method of claim 12, wherein the pharmacologically effective amount of the antibody comprises a concentration at the multiple myeloma, lymphoma, and/or leukemia tumor cells of 0.5 to 5,000 µg/ml.

14. The method of claim 12, wherein the pharmacologically effective amount of the antibody comprises a concentration at the multiple myeloma, lymphoma, and/or leukemia tumor cells of 5 to 500 µg/ml.

15. The method of claim 12, wherein the pharmacologically effective amount of the antibody comprises a concentration at the multiple myeloma, lymphoma, and/or leukemia tumor cells of 20 to 100 μg/ml.

16. The method of claim 11, wherein said pharmacologically effective amount of the antibody reduces proliferation of the multiple myeloma, lymphoma, and/or leukemia tumor cells by over 50%.

17. The method of claim 11, wherein the pharmacologically effective amount of the antibody reduces proliferation of the multiple myeloma, lymphoma, and/or leukemia tumor cells by over 75%.

18. The method of claim 11, wherein the pharmacologically effective amount of the antibody reduces proliferation of the multiple myeloma, lymphoma, and/or leukemia tumor cells by over 90%.

19. The method of claim 11, wherein the pharmacologically effective amount of the antibody binds to MHC $\beta_2$-microglobulin HLA class I molecules located on the multiple myeloma, lymphoma, and/or leukemia tumor cells.

20. The method of claim 11, wherein the pharmacologically effective amount of the antibody reduces the number of MHC $\beta_2$-microglobulin HLA class I molecules located on the multiple myeloma, lymphoma, and/or leukemia tumor cells.

21. The method of claim 11, wherein the pharmacologically effective amount of the antibody stimulates apoptosis in the multiple myeloma, lymphoma, and/or leukemia tumor cells.

* * * * *